United States Patent [19]

Rounbehler et al.

[11] Patent Number: 5,098,451
[45] Date of Patent: Mar. 24, 1992

[54] VAPOR CONCENTRATOR

[75] Inventors: David P. Rounbehler, Bedford; David P. Lieb; Eugene K. Achter, both of Lexington; Gabor Miskolczy, Carlisle; Eugenie Hainsworth, Arlington; Gregory J. Wendel, Stoneham, all of Mass.

[73] Assignee: Thermedics Inc., Woburn, Mass.

[21] Appl. No.: 81,913

[22] Filed: Jul. 8, 1987

[51] Int. Cl.$^5$ .............................................. B01D 15/08
[52] U.S. Cl. ...................................... 55/67; 436/156; 89/1.1
[58] Field of Search ........................ 436/156, 155–159; 73/1 G, 23.1, 28, 35, 167; 55/67; 89/1.1

[56] References Cited

U.S. PATENT DOCUMENTS

| | | | |
|---|---|---|---|
| 2,373,113 | 4/1945 | Francis | 23/254 |
| 3,430,482 | 3/1969 | Dravnieks et al. | 73/23.1 |
| 3,568,411 | 3/1971 | Dravnieks et al. | 55/208 |
| 3,701,632 | 10/1972 | Lovelock | 23/232 E |
| 4,023,929 | 5/1977 | Becker et al. | 23/230 PC |
| 4,053,281 | 10/1977 | Carter | 436/159 X |
| 4,166,379 | 9/1979 | Bradshaw | 73/23 |
| 4,220,452 | 9/1980 | Bray | 436/156 |
| 4,293,316 | 10/1981 | Block | 55/16 |
| 4,305,724 | 12/1981 | Micko | 436/156 |
| 4,467,038 | 8/1984 | Scott | 436/158 X |
| 4,531,398 | 7/1985 | DiBenedetto et al. | 73/1 G |
| 4,534,204 | 8/1985 | Bergquist | 73/1 G |

FOREIGN PATENT DOCUMENTS 8301512  4/1983  PCT Int'l Appl. ................. 422/89

OTHER PUBLICATIONS

Conrad, "Explosives Detection—The Problem and Prospects", possible publication, of unknown date.
Peterson, "Temperature Dependence of Adsorption Effects of Explosives Molecules", International Symposium on Analysis and Detection of Explosives, FBI Academy (1983).

Primary Examiner—Peter A. Nelson
Attorney, Agent, or Firm—Herbert E. Messenger

[57] ABSTRACT

A highly selective, sensitive, fast detection system and method are disclosed for detecting vapors of specific compounds in air. Vapors emanating from compounds such as explosives, or stripped from surfaces using heat and suction from a hand-held sample gun, are collected on surfaces coated with gas chromatograph (GC) material which trap explosives vapors but repel nitric oxide, then are desorbed and concentrated in one or more cold spot concentrators. A high speed gas chromatograph (GC) separates the vapors, after which specific vapors are decomposed in two pyrolyzers arranged in parallel and the resulting nitric oxide is detected. A low temperature pyrolyzer with silver produces NO from nitramines or nitrite esters; a high temperature pyrolyzer decomposes all explosives vapors to permit detection of the remaining explosives. Also disclosed is a series arrangement of pyrolyzers and gas chromatographs and an NO detector to time-shift detection of certain vapors and facilitate very fast GC analyses. The use of hydrogen as a carrier gas, plus unique collectors and concentrators, high speed heaters, NO detectors, and very fast, temperature-programmable GC's enhance selectivity, sensitivity and speed of detection.

20 Claims, 14 Drawing Sheets

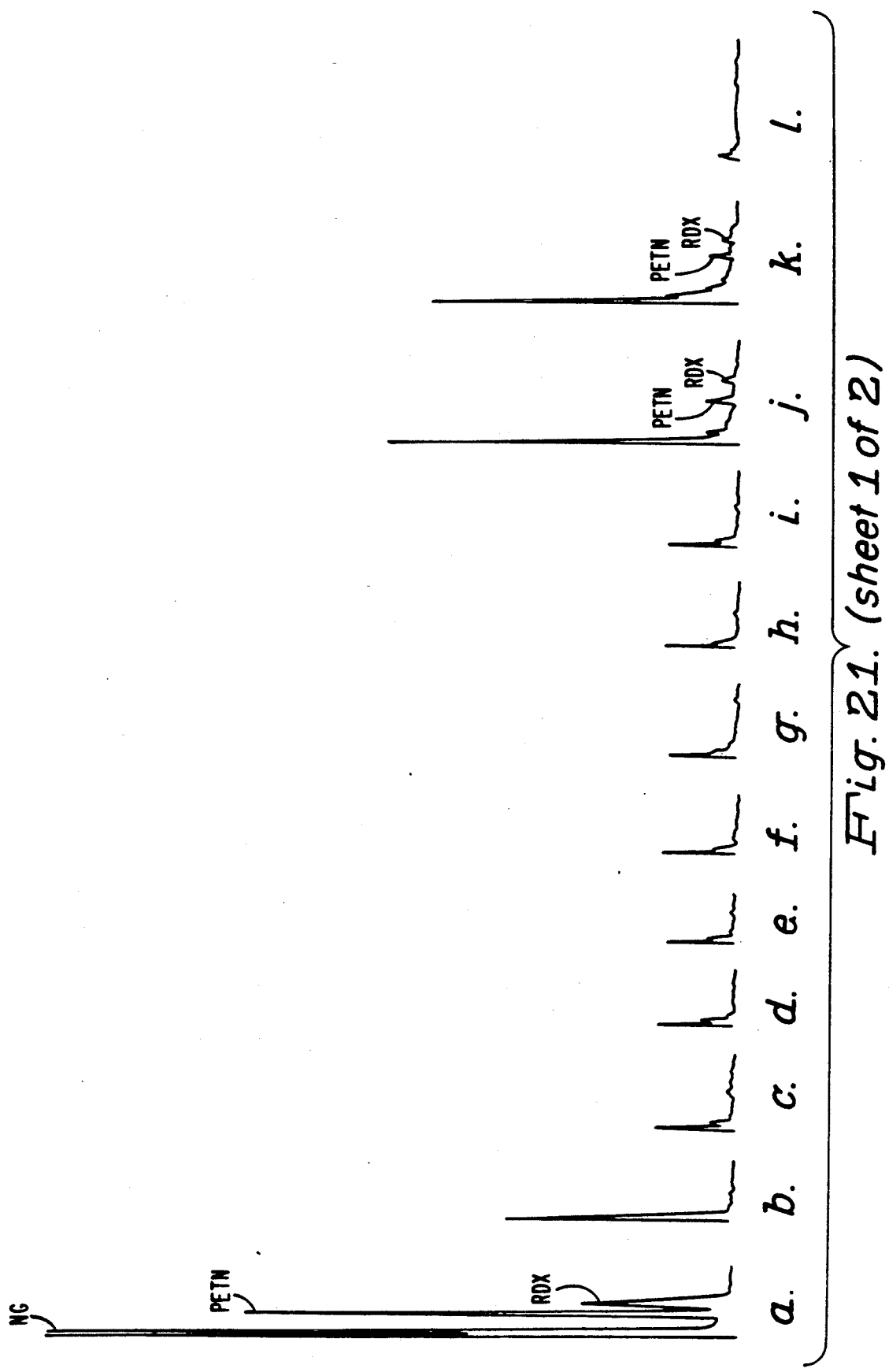
Fig. 21. (sheet 1 of 2)

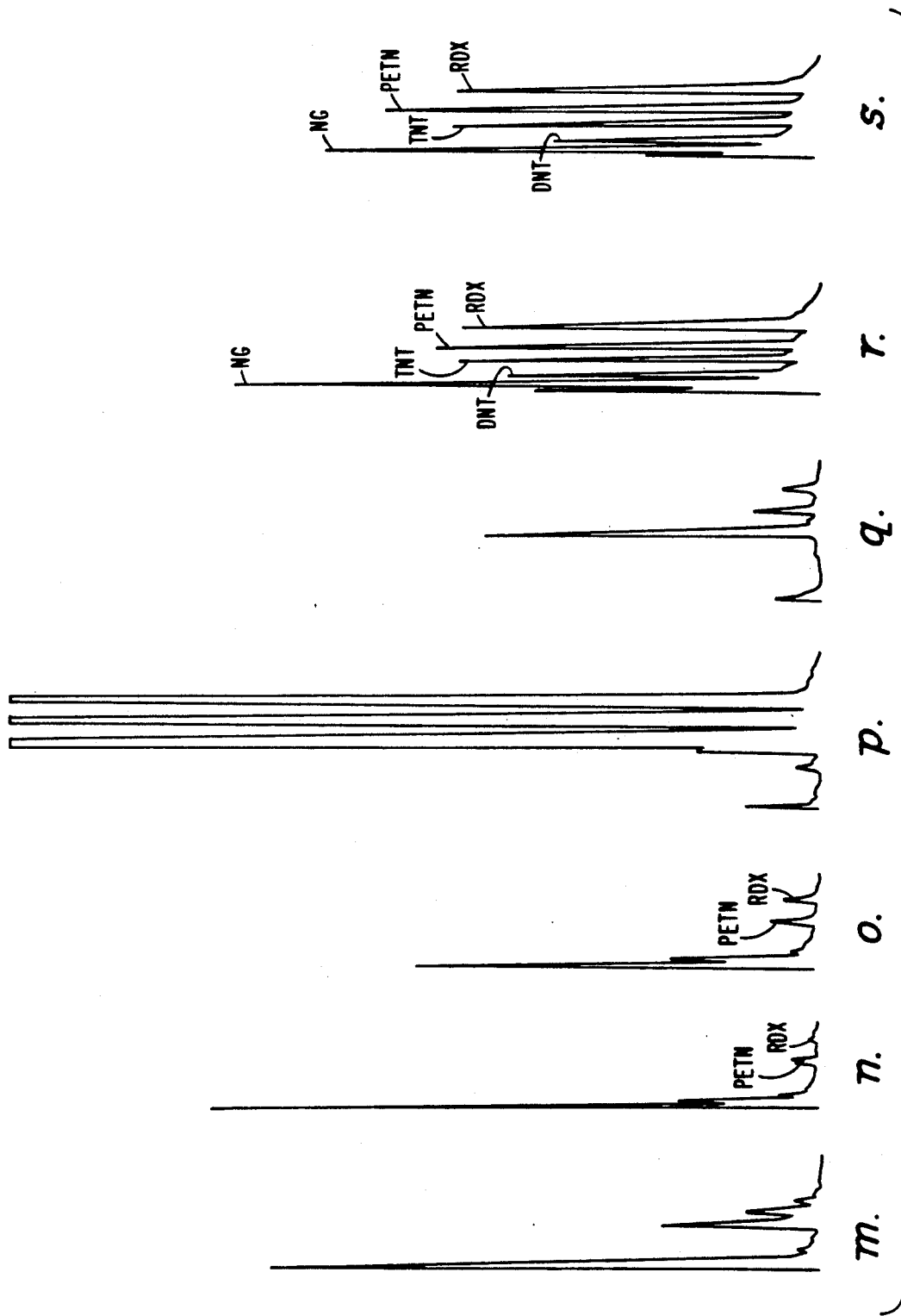
Fig. 21. (sheet 2 of 2)

VAPOR CONCENTRATOR

This invention was made with Government support under Contract No. 2038-563371 awarded by the Department of State. The Government has certain rights in this invention.

BACKGROUND OF THE INVENTION

This invention relates to selective detection of specific compounds and in particular to the concentrating of vapors, especially explosives vapors, in air samples and airborne samples acquired from surfaces.

Detection of explosives carried by persons or concealed in buildings, airplanes, cars or other locations can be vital to prevention of injuries and damage to property. However, detection by direct searching is quite costly and time-consuming, can at times be dangerous, and can also be susceptible to error. Thus, it is desirable to detect explosives somewhat indirectly, as by their presence in very small amounts of vapors in air or other gases which have been in contact with explosives in solid or liquid form.

To be effective, devices for detecting vapors of selected compounds such as explosives in air must fulfill several requirements. They must, of course, be reliable. Also, they need to be highly sensitive in order to detect the minute quantities (parts per quadrillion ($10^{15}$) or less) present in vapors and which in turn may indicate the presence of much larger quantities of the compounds. It is essential that explosives detection systems be very selective so as to prevent or minimize false alarms which would result from detection of compounds which are not explosives, and yet be highly reliable so that no explosives present are overlooked or not detected. In certain applications, such as screening persons for possession of explosives, detectors must operate rapidly—they must determine, essentially in real time, whether explosives are present—and they should also be as non-intrusive as possible. For many situations, it is important that the detector identify the specific explosive detected. Other characteristics which may be important in an explosives detector are that it be portable, rugged, and able to function in harsh environments.

Various systems are known for detecting specific compounds such as explosives, but none have provided the combination of selectivity, sensitivity, reliability, and rapid response needed for an effective and reliable detector. Systems such as electron capture detectors, mass spectrometers, ion mobility spectrometers, and nitric oxide chemiluminescence analyzers have been employed for detecting explosives, as have certain animals (notably dogs). The systems may perform satisfactorily if provided with high or moderate levels of certain explosives vapors and if allowed ample time for analysis. However, they generally are slow and also fail to provide the selectivity to distinguish explosives from various other compounds, particularly nitrogen-containing compounds, whose vapors may be present along with the explosives. The selectivity of such systems decreases as the amount of specific vapors available for detection decreases and is a significant drawback in detection of low levels of explosives. Attempts to concentrate vapors have proven time-consuming and have resulted in premature breakdown of the explosives vapors during their subsequent release for selective analysis. As a result, non-explosives such as halogenated solvents, nitrosamines, perfumes, nitrogen oxides ($NO_x$), and phthalates interfere with, and may give false readings instead of, accurate detection of explosives.

It is an object of the invention to provide apparatus for concentrating vapors of specific compounds and for releasing the vapors without decomposing them.

It is an object of the invention to provide apparatus for concentrating and releasing vapors of specific compounds without trapping oxides of nitrogen in any significant amount.

It is an object of the invention to provide apparatus for rapidly concentrating vapors received in a hydrogen carrier gas from a collector and for quickly releasing the vapors as a focussed, small volume injection to a gas chromatograph.

It is a particular object of the invention to provide a two-stage vapor concentrator for successively concentrating vapors of compounds such as explosives and for injecting the concentrated vapors into a gas chromatograph.

It is an object of the invention to provide vapor concentration apparatus which can rapidly concentrate and desorb explosives vapors to facilitate high speed, highly selective, highly sensitive detection of explosives.

SUMMARY OF THE INVENTION

The invention is a system and method for rapidly concentrating vapors of specific compounds such as explosives and for releasing or injecting the concentrated vapors into a gas chromatograph. The vapor concentrator traps vapors from a gas sample in a thin coating without trapping oxides of nitrogen. Upon being flash-heated, the coating releases the concentrated vapors for further processing, particularly high speed gas chromatographic separation and selective detection of specific compounds at high sensitivity.

In a preferred embodiment the vapor concentrator includes a cold spot, or multiple series-connected cold spots, each including a metal tube whose inner surface (or the inner surface of a glass or quartz tube extending through the metal tube) contains a coating of gas chromatograph (GC) material such as polymerized methyl silicone. Each metal cold spot tube extends through a block of metal which is cooled to maintain the tube at a selected low temperature so that the coating traps vapors from gas samples passed through the tube. A heater, such as an electrical resistance heater with connections to opposite ends of the metal tubes, flash heats the tube and the coating at selected intervals to rapidly desorb vapors into hydrogen gas which carries the concentrated vapors away for analysis.

An important application of the vapor concentrator is in rapidly concentrating explosives vapors collected from air samples and then dumping or injecting the concentrated vapors into a small bore, high speed gas chromatograph. In one arrangement wherein a two-stage cold spot concentrator forms part of a system for detecting airborne explosives vapors, each cold spot is connected to a six-port valve which in turn is also connected to a source of hydrogen carrier gas and a collector/desorber assembly. With the valve in a first position hydrogen delivers a gas sample at a relatively high flow rate to the first cold spot for trapping of vapors, with the remaining flow vented to atmosphere or passed to a vacuum pump. When the valve is switched to a second position, hydrogen passes successively through both cold spots at a lower flow rate. At selected times vapors are flash-heat-desorbed from the first cold spot, trapped and further concentrated in the second cold spot, then flash-heat-desorbed from the second cold spot and injected in a very small volume of hydrogen into a gas chromatograph. The invention provides a high speed technique for substantially increasing vapor concentrations, without decomposing specific vapors of interest, and while eliminating oxides of nitrogen and certain other potential interferents with detection of specific compounds.

BRIEF DESCRIPTION OF THE DRAWINGS

FIG. 21 shows several chromatograms resulting from analysis in an NO detector of the products of decomposition of gas samples of known composition in a low temperature or high temperature pyrolyzer.

DETAILED DESCRIPTION

Detection of vapors such as explosives, as disclosed herein, is based on trapping and concentration small amounts of vapor given off by explosives or stripped from surfaces contaminated by trace amounts of explosives, decomposing the concentrated vapors to produce nitric oxide gas (NO), and then detecting the NO from the decomposed vapors. It is essential to and a major feature of the vapor detection system that it is highly selective. Even when used to monitor air samples containing minute quantities of explosives (1 part in $10^{14}$ or less) and considerably higher concentrations of nitrogen oxides and non-explosives which could yield NO upon heating, the detector systematically avoids response to all compounds which are not of interest and correctly identifies the explosives.

The vapors trapped and detected according to the techniques and apparatus disclosed herein may be in the gas phase, or adsorbed on small (microscopic) particles, or dissolved in aerosol droplets. The surfaces described collect not only vapor in the gas phase but the particulates and aerosol droplets as well, and the term "vapors" as used herein refers to vapors collected in any of these forms.

Explosives to be monitored all contain nitrogen, and most include one or more nitride ($-NO_2$) functional groups, typically attached to a carbon, nitrogen, or oxygen atom. Examples of explosives of interest are trinitrotoluene (TNT), dinitrotoluene (DNT), nitroglycer (NG), pentaerythritol tetranitrate (PETN), ethylene glycol dinitrate (EGDN), cyclotetramethylene tetranitramine (HMX), cyclo 1, 3, 5-trimethylene-2, 4, 6-trinitramine (RDX), and water gels (ammonium nitrate plus additives).

Figure 1:
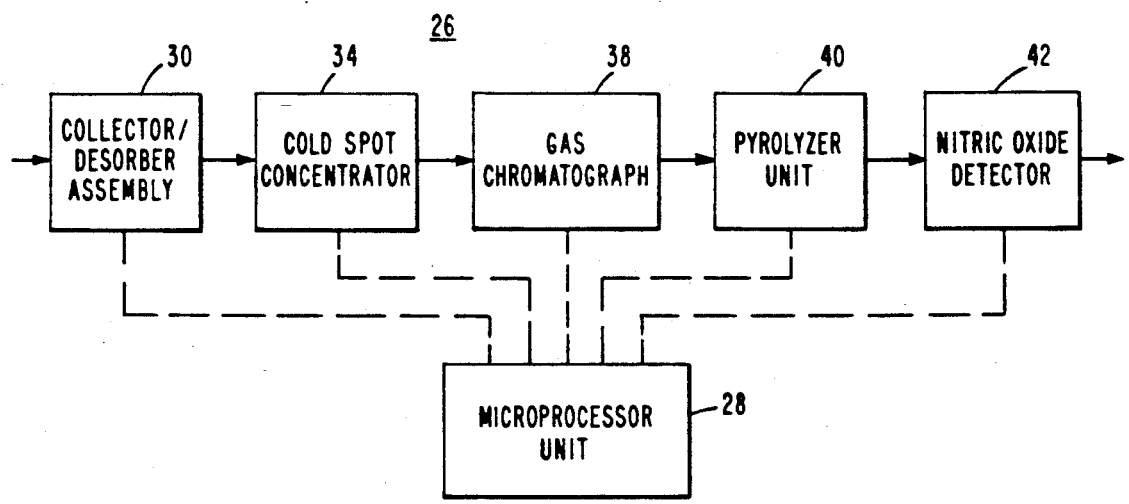
FIG. 1 is a schematic diagram of an vapor detection system showing its principal subsystems.

A preferred vapor detector system, shown schematically in FIG. 1, includes five subsystems which are connected in series and linked to a microprocessor unit 28 containing one or more microprocessors which controls their operation in rapid, highly selective and sensitive detection of vapors, such as explosives vapors, in air samples. The principal subsystems in addition to the microprocessor unit 28 are: (1) a collector/desorberassembly 30 employed to trap and then desorb vapors from an air sample, (2) A cold spot concentrator 34 comprising one or more series-connected cold spots used to successively concentrate vapors desorbed from a collector, (3) a short, high speed gas chromatograph 38 for rapidly separating different substances, including vapors of specific compounds of interest, in the sample according to their calibrated retention times; (4) a pyrolyzer unit 40 for decomposing selected vapors to produce nitric oxide gas (NO); and (5) a highly sensitive nitric oxide detector 42 which detects NO and produces signals for analysis and appropriate warning of the presence of selected compounds such as explosives. The construction and operation of each of the major subsystems is described in detail hereinafter in connection with detection of explosives, it being understood that many of the principles disclosed are applicable to detection of vapors of other specific compounds, particularly other nitrogen-containing compounds such as cocaine and heroin.

Collection/Desorption

A collector is included in the preferred detector system 26 chiefly to provide increased sensitivity of the instrument and also to assist in separating explosives vapors from potential interferents such as nitrogen oxides ($NO_x$) often present in air samples. Trapping of vapors given off by, or stripped from, explosives (vapors which may be present at concentrations of one part in $10^{14}$ or lower) concentrates the available vapors so that, when combined with further focussing in cold spots, vapor concentrations are obtained which are sufficent for detection in a nitric oxide detector. For example, an ozone-based chemiluminescence analyzer employed as the preferred nitric oxide detector 42 has a sensitivity level of about one picogram ($10^{-12}$ g.) of NO, as defined by the amount of NO requiredto give a response five times greater than the level of noise. This is equivalent to a sensitivity to RDX of about 2.5 picograms of RDX. If 2.5 picograms of RDX were decomposed in the pyrolyzer unit 40 to produce NO, the nitric oxide detector 42 would produce a response five times greater than the noise level. To obtain RDX and other explosives vapors in amounts sufficient for such detection, the detector system 26 employs a sample collector as disclosed in the following paragraphs.

A key aspect of the collector/desorber assembly 30 is a surface which (1) will effectively extract or trap explosives vapors from a gas sample, typically an air sample, as the sample is flowed over the surface at a selected temperature such as room temperature; (2) will repel or not effectively trap NO or $NO_2$ present in the gas sample, and (3) will release or desorb the explosives vapors without their decomposition when heated and under the flow of a gas such as hydrogen. A preferred surface is a coating of an organic silicone polymer such as a polymerized methyl silicone or polymerized methyl/phenyl silicone normally employed in a gas chromatograph column. Such coating materials have a three dimensional structure which entraps specific compounds such as explosives by both chemical and physical means. This effect is dependent upon both the actual polymer being employed and the temperature of the polymer.

Figure 2:
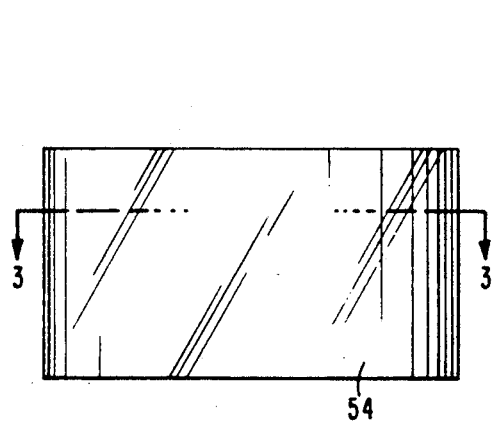
FIG. 2 is a side view of a sample collector having a bundle of coated tubes for trapping explosives vapors.
Figure 3:
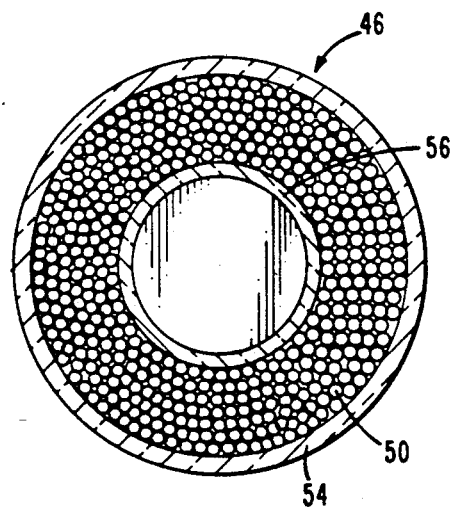
FIG. 3 is a cross-sectional view of the sample collector taken along the line 3—3 of FIG. 2.
Figure 4:
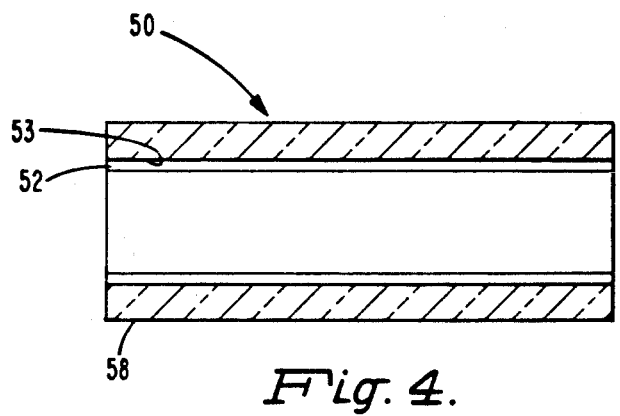
FIG. 4 is a single tube of a collector enlarged to show various coatings on its surfaces.

One preferred collector 46, illustrated in FIGS. 2 and 3, is a cartridge containing a bundle of small diameter quartz tubes 50 whose inner surface is coated with a thin layer of the gas chromatograph (GC) material and which are closely packed in an annulus between an outer glass ring 54 and an inner glass piece 56. Application of mass transfer theory permits appropriate selection of tube diameter, tube length, and flow rates for high collection efficiency at manageably low pressure drop. Tubes 50 having an inner diameter of about 0.53 mm, an outer diameter of about 0.8 mm and a length of about 19 mm have been found to be suitable, with flow and mass transfer calculations showing that at a sample flow rate of about 130 cm³ per minute through a collector containing 400 such tubes, at least about forty percent of the gas molecules in the sample will contact the inner wall, and thus the GC material 52, of such tubes. A typical tube bundle with about 400 tubes 50 may have the tubes packed between a Pyrex glass ring 59 having an outer diameter of 32 mm and an inner diameter of 28 mm and a Pyrex glass inner piece or center support 56 with closed ends having an outer diameter of 22 mm. Each tube 50 (see FIG. 4 showing a single tube enlarged to illustrate various coatings) has a layer 52 of GC material of thickness about 0.1 to 5 microns, typically 1-2 microns, on its inner wall. Preferred GC materials are a polymerized methyl silicone polymer known as DB1 or a polymerized methyl silicone known as DB5, available from J & W Scientific, of Folsom, Calif., and methyl/cyano silicones. The GC material may be applied over a base coating of a dielectric material such as silicon dioxide or silicon, preferably a thickness about 0.01-0.1 micron. The base or inner coating 53, which may not be needed for coating quartz or glass tubes but may be required when the GC materials are applied to metal ribbons or metal tubes, as described hereinafter, also acts as a wetting agent to promote adherence of the GC layer 52. A preferred method of applying the base coating 53 is to flow chlorosilane and toluene through the tube 50 and then flush with methanol. The layer of GC material may be applied by aerosol spraying or by sealing one end of a tube, filling the tube with the liquid GC material, and applying a vacuum.

The tubes 50 may also have a thin coating 58 of optical grade silicone on their outer wall, to increase their strength and flexibility for bending, which may be useful in coiling the tube for application of other coatings prior to cutting the tubes to size, and the same optical grade silicone material may be used to glue the tubes 50 in place during assembly. The silicone coatings 58 on the outer wall of the tubes 50 may be doped with a small amount (e.g., 0.5%) of carbon black to increase absorption of infrared radiation used to heat the GC material 52 during desorption of explosives vapors from it.

Figure 5:
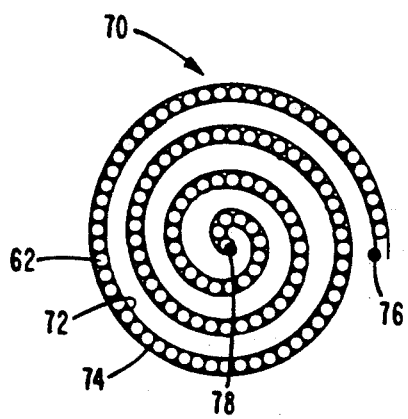
FIG. 5 is an end view of a sample collector having a metal bundle of coated tubes in contact with a spiral-wound metal foil.
Figure 6:
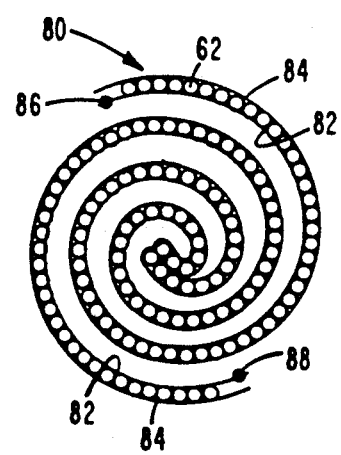
FIG. 6 is an end view of a sample collector having a bundle of coated tubes in contact with a metal foil wound in a double spiral.
Figure 7:
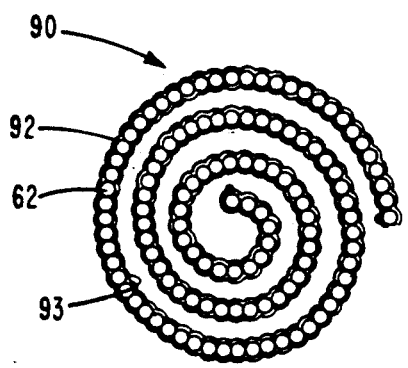
FIG. 7 is an end view of a sample collector having a bundle of coated tubes in contact with a spiral wound metal foil which is corrugated to permit increased packing density.

Alternate sample collectors utilizing arrays of tubes 62 are illustrated in FIGS. 5, and 6, and 7, which, for clarity, show portions of collectors in an intermediate stage of formation—that is, tubes packed far less densely than the finished collector, and without stiffeners and radial support members which may be required in the collectors. All three arrangements include tubes 62, similar to the tubes 52, whose outer walls are in contact with a thin metal foil so that each tube 62 and the layer of GC material on its inner wall may be indirectly heated by passing an electrical current through the foil. FIG. 5 shows a collector 70 with a metal foil 72 and an electrically insulating sheet 74 wrapped in a spiral and sandwiching between them a spiral "line" of collector tubes 62. The foil may be formed of stainless steel or other suitable metal about 0.01 mm in thickness with one side coated with adhesive to insure good thermal contact between the foil 72 and the tubes 62. The sheet 74 may be Teflon tape. Electrical leads 76 and 78 are attached to both ends of the foil 72 so that a suitable power source may be connected to the foil to deliver electric current and heat the foil 72, in turn heating the layer of GC material to desorb explosives vapors trapped by the layer 68.

In the sample collector 80 of FIG. 6 a metal foil 82 and insulating sheet 84 are wrapped in a double spiral. This permits both electrical leads 86 and 88 to be positioned on the outside of the spiral-shaped collector 80, facilitating connection of an electrical power source to the collector 80.

FIG. 7 illustrates a sample collector 90 wherein a metal foil 92 includes corrugations each shaped to closely fit around a portion of an individual tube 62, with corrugated insulation 93 on the opposite side of each tube. This provides a packing density of the tubes 62 somewhat higher than that of FIGS. 5 and 6. Packing density may also be increased with corrugated or uncorrugated foils—by arranging the tubes 62, which are electrically insulating, so that they isolate successive turns of the foil, eliminating the need for an insulating sheet.

Figure 8:
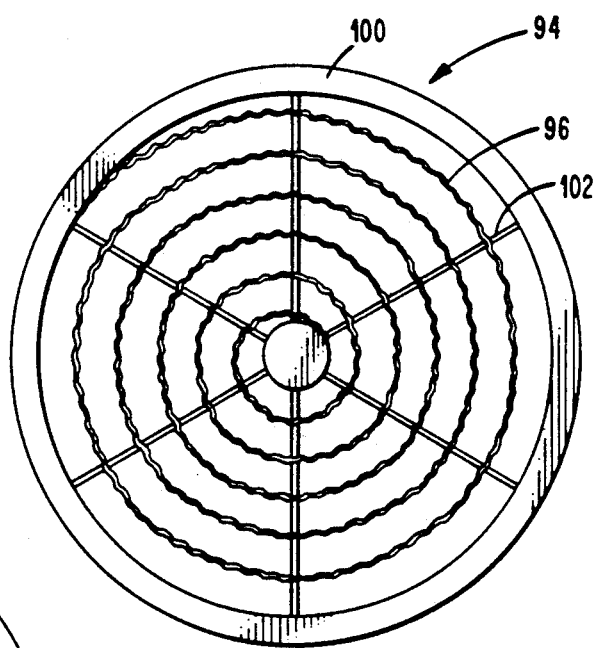
FIG. 8 is an end view of a spiral wound sample collector utilizing a metal ribbon as a substrate.

Sample collectors for the explosives detector system of the invention may, instead of utilizing electrically insulating tubes in the collection of vapors, employ electrically conductive substrates coated with GC material. Such collectors may be less expensive to fabricate than tube bundles, and they allow rapid desorption of sample vapors at relatively low electrical power since their GC materials may readily be heated by passing an electrical current through the substrate. One suitable collector 94 with a metallic substrate, illustrated in FIG. 8, includes a metal ribbon 96 coated on both sides with a layer of GC material formed into a high surface area, gas pervious structure such as a narrowly-spaced wound spiral which is mounted with a tube 100. Appropriate spacers such as non-conductive radial spokes 102 may be included and the ribbon may be corrugated to provide addition surface area. The ribbon 96, which is formed, for example, of molybdenum foil about 0.002 cm thick, preferably has a base layer of dielectric material of 0.01–0.1 microns thickness such as silicon dioxide or silicon applied to both sides (as by sputtering, chemical vapor deposition, or other suitable technique) prior to application of the GC material to promote adhesion of the GC material and to prevent vapors trapped in the coating from passing to the metal ribbon and tightly adhering to it. A suitable thickness for the GC material is 1-2 microns, and the GC materials may be applied by aerosol spraying or other suitable technique. Explosives vapors in air samples passed through the tube 100 contact the GC material 98 and are trapped by it, and electrical resistance heating of the ribbon 96 subsequently releases the vapors for further processing in the explosives detector system 26.

Figure 9:
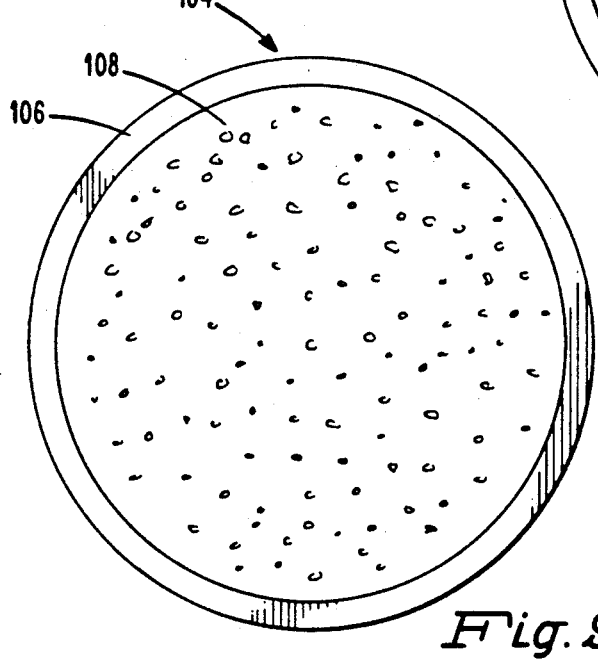
FIG. 9 is an end view of a sample collector which includes a porous frit as the substrate.

Another sample collector 104 with an electrically conductive substrate, shown in FIG. 9, comprises a porous fritted material such as nickel which is coated with a suitable GC material and which may be mounted in a metal tube 106. Collection of vapors occurs as a gas sample is pulled through the frit 108, and the frit 108 also filters particulate matter from the gas stream, thus preventing such particles from being introduced into downstream portions of the explosives detector system. The frit 108 may, if electrically conductive, be heated for subsequent desorption of the vapors by passing an electrical current through it or through the tube 106 with which it is in contact. It may also be possible to desorb the vapors by passing heated carrier gas through the porous frit.

The above-mentioned sample collectors may comprise a bundle of identically coated ribbons or frits. Alternatively, some tubes or a portion of the ribbon or frit may have coatings of different materials and/or thicknesses as to selectively collect and release different explosives. For example, coatings of high polarity may be required to trap explosives having high vapor pressures (e.g. EGDN and NG), while coatings of lower polarity are adequate to trap explosives of low vapor pressure (e.g. TNT and RDX) which stick easily. Typically, the high polarity coatings cannot be used exclusively, however, because during subsequent desorbtion such coatings may not release the low vapor pressure explosives unless heated to temperatures at which such explosives decompose. Because the high vapor pressure explosives will usually be present at much greater concentrations than low vapor pressure explosives, only a small portion of the collector (e.g., a few percent of the tubes in a bundle) need be tailored to collect vapors of the high vapor pressure explosives.

Any of the above-described collectors may be mounted within an air-tight collection/desorbtion chamber which is connected to cold spot concentrators and in turn to other portions of the explosives detection system. In such an arrangement, for example, with the collector installed in a booth for screening people for possession of explosives or specific drugs, the collector remains in one position both while a gas sample is directed through the collector for trapping of explosives vapors, and thereafter while the collector is heated and a suitable carrier gas is passed through it for desorption of explosives vapors. Alternatively, the collector may be mounted in a hand-held sampler during sample collection and then transferred to a desorption chamber for further processing in the remaining subsystems of the explosives detector system. The provision of a hand-held sampler or sample gun permits sampling in remote areas which might otherwise be inaccessible to the explosives detector system and allows sampling of vapors by lifting or stripping from objects (e.g., surfaces) as well as sampling of vapors which are airborne due to the vapor pressure of explosives.

Figure 10:
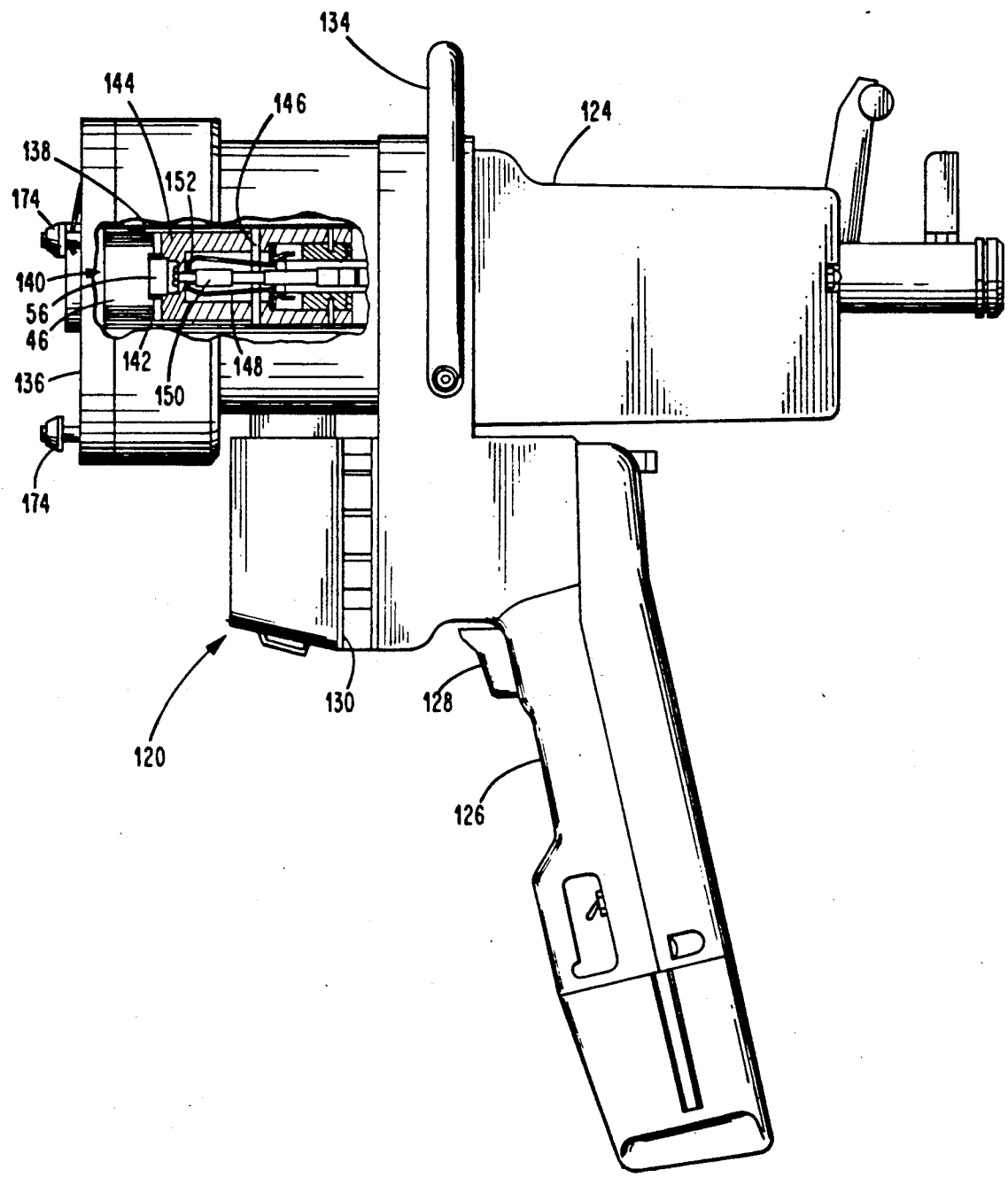
FIG. 10 is a side view of a hand-held sampler or sample gun for collecting vapors showing a collector assembly within the gun.
Figure 11:
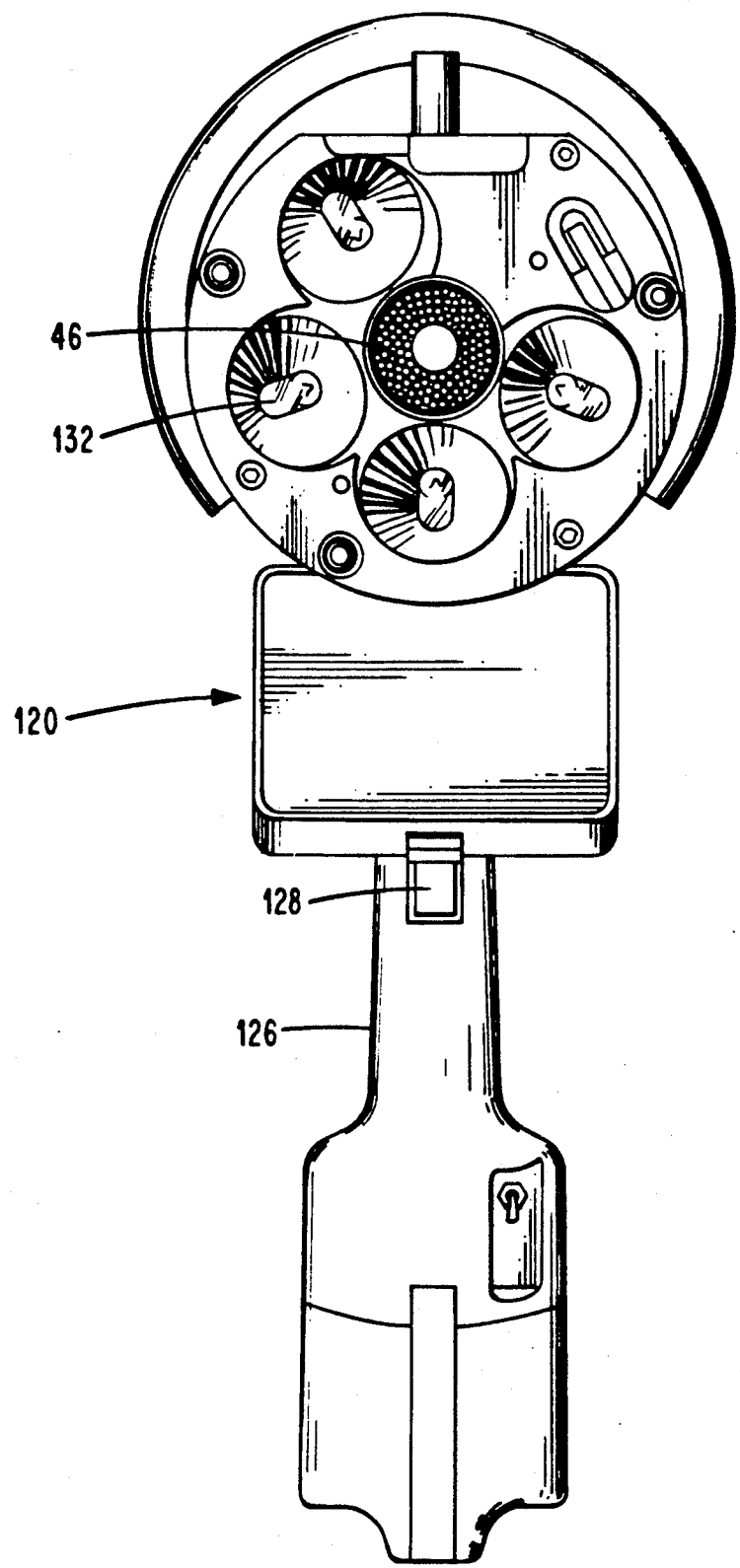
FIG. 11 is a front end view of the sample gun of FIG. 9.
Figure 12:
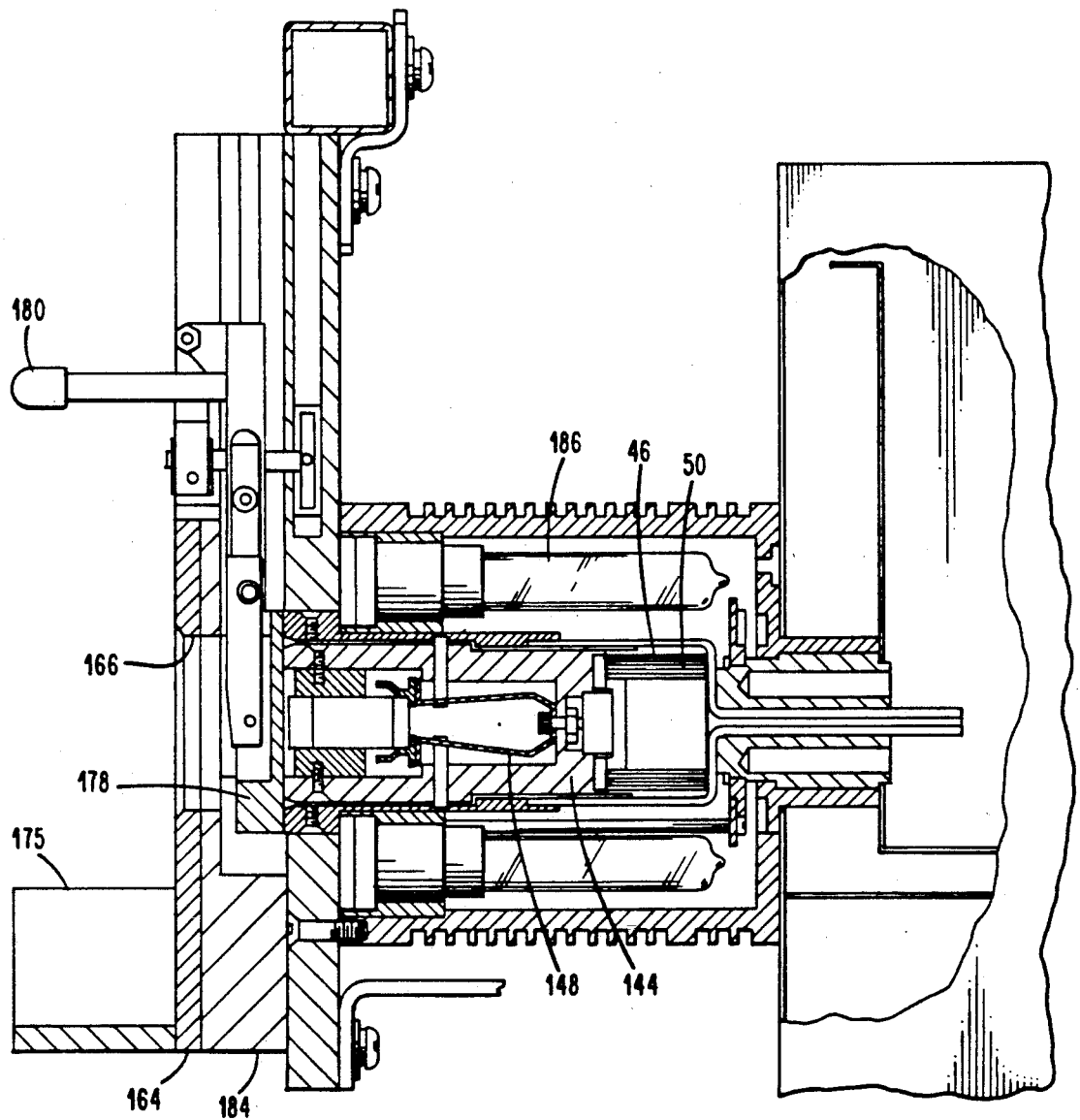
FIG. 12 is a side view of a sample collector/desorber assembly of the detector system with a collector assembly held therein.

A preferred hand-held sampler (FIGS. 10-11) is a portable gun 120 which contains rechargeable batteries within and near the rear of a barrel-like housing 124 and which may also be plugged into a suitable source of electrical power. Attached to the housing 124 is a pistol-grip handle 126 with a trigger 128 to operate a blower 130 and also to activate lamps 132 mounted in the inlet (FIG. 11) of the gun. A top ring handle 134 is also provided to assist a user in holding the gun 120. The front end of the housing 124 terminates in a flared inlet 136 which leads to a central bore 138 for receiving a sample collector assembly 140, as is shown loaded within the gun 120 (FIG. 10). A preferred collector assembly 140 includes a cartridge-like collector, such as the coated glass tube bundle 46 of FIGS. 2 and 3, attached to a body structure 142 which facilitates use of the collector, particularly its insertion into, and removal from, the gun 120 and a collector/desorber assembly 30 (FIG. 12). The body structure 142 includes a hollow body cartridge 144 to which the collector 46 is attached, as by gluing the central support 56 of the collector 46 to the cartridge 144, and locking pins 146 and a spring-pin activator 148 are also attached to the body cartridge 144 to permit loading of the collector assembly 140 within, and its removal from, the gun 120 and the collector/desorber assembly 30.

The central bore 138 of the gun 120 communicates with a blower 130 which draws air samples through the collector 46, and it may be desirable, through not illustrated herein, to utilize the exhaust of the blower 130 to form air jets which may be directed at a surface to aid in heating the surface and dislodging vapors from the surface. Extending into the bore 138 from the rear of the gun 120 is an extraction rod 150 which is used to move the collector assembly 140 into and out of the bore 138. For example, movement of the rod 150 within the hollow portion of the body cartridge 144 and towards the inlet of the gun 120 causes the rod to push against an adjustable shoulder 152 extending through an end portion of the body cartridge 144 so that the collector assembly 140 is pushed out of the gune 120.

Operation of the blower 130 is controlled by the trigger 128 on the pistol-grip handle, which may be a double or two-position trigger to permit separate activation of the blower 130 and of the array of lamps 132 mounted in the inlet 136 of the gun 120. The lamps 132, which may comprise four gold-plated projection bulbs, aid in acquisition of samples. In particular, the lamps 132, when activated for a brief interval of time such as 0.2 seconds near an object to be sample—e.g., a surface contaminated with trace amounts of explosives—heat the surface of the object which raises the vapor pressure of any explosives thus heated and may also vaporize moisture or water containing explosives particles. Action of the lamps 132, together with the blower 130, desorbs and strips explosives vapors from the surface without decomposing the vapors, and the explosives vapors are drawn into the gun 120 and trapped within the collector 46.

With regard to heating provided by the lamps 132, other suitable means for heating surfaces include hot air jets, high speed flash lamps (whose very rapid heating may avoid loss of heating by conduction by a metal surface), irons which heat by direct contact, and microwave devices. Heating of explosives on a surface increases their vapor pressure significantly (e.g. up to a factor of ten for each 10° C. increase) and blowing onto, or locally vibrating the surface (e.g., ultrasonically), can help dislodge small particles of explosives which may be collected, then later desorbed as vapors.

It has been found during sample collection from surfaces that a "void" or inactive area exists directly underneath the collector—i.e., in line with the central bore 138 of the sample gun 120—and that little or no vapor may be collected from that inactive area. Essentially all of the air which is sucked into the gun is drawn along the target surface and then into the collector 46 rather than into the collector from points directly below it. Hence, the gun 120 has been found much more effective when used in an "asymmetric surface sampling" mode wherein the gun bore is aimed at an area immediately adjacent to the specific target area (e.g., a fingerprint) and the lamps 132 heat the target. Vapors then may be drawn from the heated target area along the surfaces and up into the collector 46.

Figure 13:
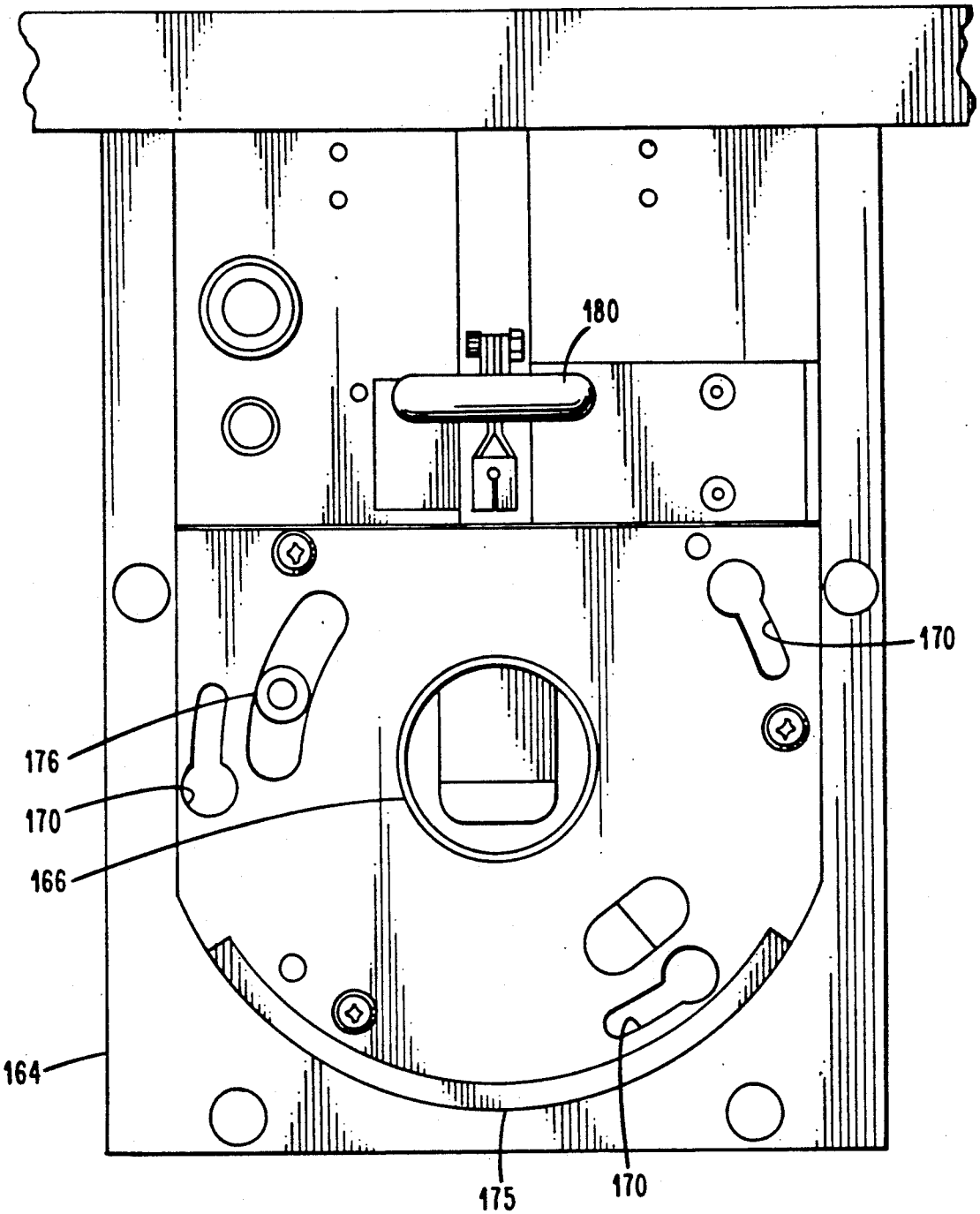
FIG. 13 is a front view, partly broken away, of the sample collector/desorber assembly of FIG. 12 illustrating its front mounting plate.

After an air sample has been drawn through the sample gun 120 and explosives vapors trapped in the collector 46, the collector is transferred to a desorption chamber 160 (FIG. 12) formed in the collector/desorber assembly 30. To facilitate direct transfer of the collector 46 from the sample gun 120 to the desorption chamber 160, the collector/desorber assembly 30 may include a front mounting plate 164 (FIG. 13). The plate 14 has an opening 166 to admit the collector 46 and contains recesses 170 which mate with pins 174 protruding from the front of the sample gun housing 124 so that the gun 120 may be locked to the plate 164 during transfer of the collector to the desorption chamber 160. The plate 164 may have a saddle 175 extending from a lower portion thereof to support the gun 120 and may also include electrical contacts 176 to permit recharging of batteries within the gun while the gun is attached to the plate 164. A slidable cover 178 is positioned behind the front mounting plate 164 and may be moved by a lever handle 180 to block the opening 160 and seal the desorption chamber 160 after a collector has been unloaded from the sample gun 120.

As an alternative to transferring the collector cartridge from the sample gun to the desorption chamber 160, the gun and collector may remain together and be loaded into the desorption chamber as a single unit for desorption and futher processing of explosives vapors. Advantages of this arrangement may include a less complex design and faster, more reliable operation.

Following transfer of a vapor-loaded collector 46 from the sample gun 120 to the desorption chamber 160 (or the drawing of an air sample through the collector while the collector is positioned within the desorption chamber 160), the GC material in which the explosives vapors are held is rapidly heated to a suitable temperature, e.g. 160-200 degrees C., to desorb the vapors from the collector for passage in a carrier gas to a cold spot 34 connected to the downstream end of the collector/desorber assembly 30. With reference to FIG. 12, the carrier gas may enter the desorbtion chamber 160 through holes or channels formed in the front plate 184 and then pass through holes in the body cartridge 144 to then flow through the collector 46. One method of heating the GC materials is to preheat the carrier gas which is input to the desorption chamber 160 from a suitable supply 182 (FIG. 16) and then is directed through the collector 46 and into the cold spot 34. This technique is suitable regardless of the type of material employed as a substrate to which the GC materials of the collector has been applied, but may be rather inefficient and time-consuming. If a conductive substrate such as a metal ribbon or metal frit is used as a collector substrate, then electrical resistive heating may be employed. If a light-transmissive collector is employed, such as a bundle of quartz tubes, then high intensity infrared radiation is preferred for heating the GC material. The infrared radiation may, as illustrated in FIG. 13, be furnished by an array of lamps 184 such as eight 500-watt lamps spaced around the periphery of a 9 cm I.D., 15 cm long tube forming the desorption chamber 160. Radiation from the lamps 184, whose absorption may be enhanced by use of a small amount (e.g., 0.5%) of carbon black in the optical coating applied to the outside of each tube 50, rapidly heats the collector tubes to a selected temperature in the range of about 160°-200° C., preferably 170° C. At these temperatures and during a time period of about 20 seconds the explosives vapors are desorbed from the GC material of the collector without decomposition and are swept away by a carrier gas such as hydrogen flowing through the tubes and pass into a cold spot 34 connected to the collector/desorber assembly 30. The desorption also decomposes labile nitrogen compounds such as peroxyacetyl nitrate which might otherwise interfere with detection of explosives. Any nitric oxide gas produced by such decomposition passes through the remaining portions of the detector system 26 prior to the decomposition and detection of explosives.

It should be noted that the direction of flow of carrier gas through the collector 46 during desorbtion is opposite to that of airflow during sample collection. Such backflushing avoids having to push through the entire collector any dirt or other contaminants trapped near its inlet during sample collection.

COLD SPOT CONCENTRATION

The second principal subsystem of the explosives detector system 26 is a cold spot 34, or two or more cold spots of connected in series. These items, termed "cold spots" because they are cooled and generally held at or below room temperature except during desorption events, function to further concentrate explosives vapors of a sample so that essentially all of such vapors may be input to a high speed gas chromatograph of predetermined capacity in a single "injection" of very small volume e.g., of about one to ten microliters. Each cold spot 34 preferably comprises one or more metal tubes whose inner wall contains a layer of GC material which may be similar to that employed in the sample collector 46 and which may be applied over a base coating of silicone dioxide or other dielectric material. Alternatively, the metal tube of each cold spot may have threaded therethrough a section of gas chromatograph column coated with a GC material. The GC material, when kept cool—e.g., at about 40° C. or less, preferably in the range of about −10° to 20° C.—removes and traps vapors of specific compounds such as explosives and the drugs cocaine and heroine from a mixture of carrier gas and vapors received from the collector/desorber assembly 30. Subsequent flash heating of the cold spot tube as carrier gas is passed through it desorbs the explosives vapors without their decomposition so the vapors flow to the next cold spot and eventually to the analytical column of the high speed gas chromatograph 38.

Figure 14:
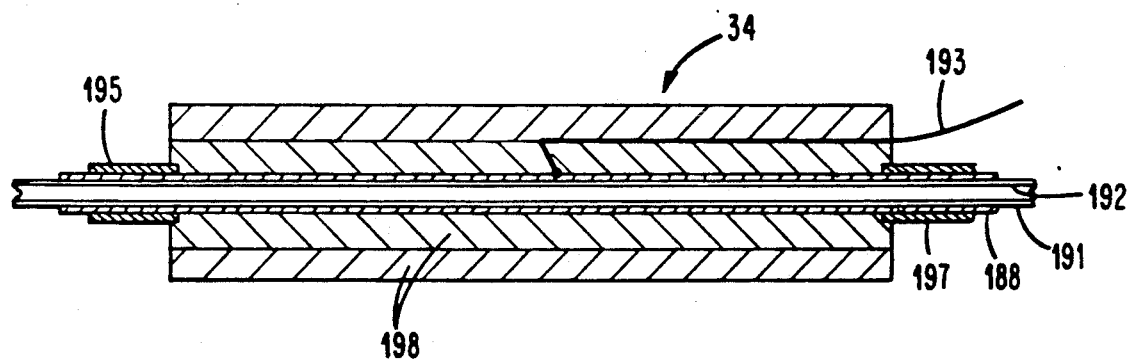
FIG. 14 is a side view of a cold spot for concentrating vapors following their collection.

A suitable construction for one stage of a cold spot 34 (FIG. 14) includes a stainless steel tube 188 of 1.6 mm outer diameter (OD) and 0.99 mm inner diameter (ID) and having a section of 0.53 mm ID Megabore GC tubing (available from J & W Scientific) threaded through it. The GC tube 191 may be lined with a monolayer of silicon dioxide (e.g. of thickness about 0.0001 micron) and has a coating 192 of GC material of thickness from 0.1 to 5 microns, typically 1-2 microns. The tube 191 may have a working length of about 10 cm thus an internal volume of about 22 mm$^3$.

A cold block 196 (FIG. 15) of aluminum surrounds the tube 188 and is maintained at a constant temperature such as about 10° C. by a suitable cooler device such as a thermoelectric cooler 190, a commercially available, device utilizing semiconductor materials and without moving parts which provides cooling when an electrical current is passed through it. The portion of the tube 188 inside the cold block 196 is wrapped with one or more layers of insulation 198 such as silicone rubber, two layers being shown in FIG. 14, which isolate the tube 188 electrically from the cold block 196. The insulation 198 also provides thermal resistance so that heat supplied to the tube, for desorption of explosives vapors will be conducted rapidly to the GC material 192 but only slowly to the cold block 196. A thermocouple 193 may also be connected to the tube to sense temperature for control during desorption.

A preferred method of flash-heating the cold spot tube 188 and thus the GC tube 191 to apply a voltage between its opposite ends and resistively heat the tube. For this purpose the ends of the tube 188 which extend from the cold block 196 may have nickel sleeves 195 and 197 crimped around them and connections made from the sleeves to a source of electrical power. Care must be exercised in constructing the cold spot, as in making sure the sleeves 195, 197 extend to or slightly within the cold block 196, so that the tube is rapidly and uniformly heated to the desired temperature during desorption. Excess heating (hot spots) in the tube 188 could result in partial decomposition of certain explosives while local cool regions can result in incomplete removal of explosives. Both alternatives are to be avoided since decreased sensitivity of detection would result.

The flash heater may be constructed and operated to initially apply a relatively high voltage across the tube 188 to quickly raise its temperature and then after a preset time interval to switch to a lower voltage so as to maintain the tube temperature at a desired level. Alternatively, a thermocouple such as the thermocouple 193 (FIG. 14) may be attached to the tube 188 and interact with an appropriate control circuit to maintain predetermined temperatures. A third technique is to control temperature based on measured resistance of the metal tube 188 itself, as by applying AC or DC power to the tube 188 through a solid state switch which is periodically opened for a short time to allow a small sensing crrent to flow to the tube, and measuring the voltage drop due to the sensing current. A temperature in the range of about 150-200 degrees C., typically 170° C., has been found suitable for desorbing explosives without decomposing then, the desired temperature being a function of flow rate through the tube 191 and the specific vapors to be desorbed. After the heating and desorbtion of explosives vapors into a carrier gas has been completed, e.g., over a time interval of 0.01-15 seconds, the voltage applied to the tube 188 is discontinued, allowing the cold block 196 to cool the tube 188 and tube 191 down to the cold block temperature for the next trapping of vapors in the tube 191.

One or more additional cold spot tubes may be connected in series with the cold spot tube 188, each successive cold spot tube preferably having a smaller internal volume so as to provide progressively increasing concentration of the vapors as they are moved from one cold spot tube to the next. If two cold spots are used, the second cold spot may be a section of the analytical column of the gas chromatograph 38 threaded through a stainless steel tube.

Figure 15A:
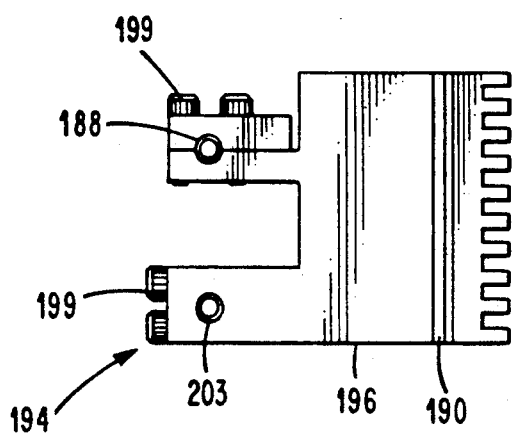
FIGS. 15(a) and 15(b) are an end view and a side view respectively, of a cold block and cooler assembly for two cold spot concentrators.
Figure 15B:
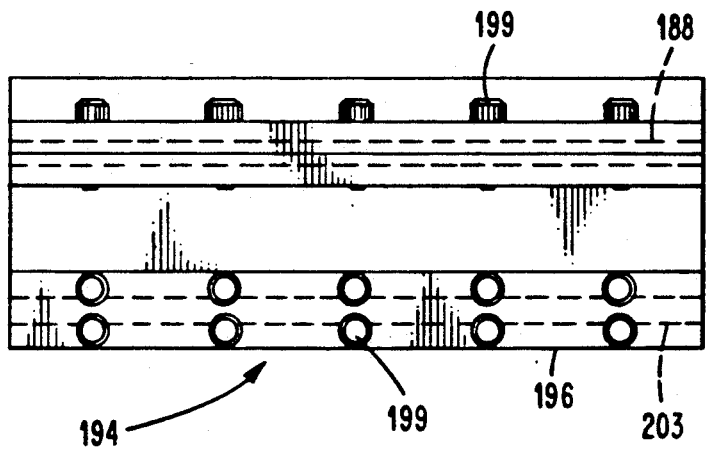

FIGS. 15(a) and 15(b) show an end view and side view, respectively, of two cold spot tubes 188 and 203 which extend through a double cold block assembly 194 which includes a cold block 196 and plates 197 and 199 removably fastened to the block 196 by bolts 199. For clarity, the tubes 188 and 203 are shown in FIG. 15 without their surrounding insulative wrappings, it being understood that the portions of both tubes 188 and 203 which extend through the block 196 include wrappings similar to those shown as 198 in FIG. 14. The tube 203, may have a GC tube 200 of an inner diameter of about 0.32 mm and a working length of about 10 cm threaded through it, and the GC tube 200 includes a suitable coating of GC material which may be the same as that of the tube 191 of the first cold spot. Tubes 188 and 203 are connected in series externally of the cold block 196, as by glass-lined stainless steel tubes, and each is connected to a separate flash heater (not shown) to move explosives vapors in successive steps from tube 191 to tube 200 and then into a gas chromatograph connected to the tube 190. Preferably the cold block 196, and tubing external to it, are enclosed in an oven 202 (see FIGS. 16(a), 16(b)) operated to maintain a temperature of about 150 degrees C. in the tubes external to the cold block so that explosives vapors do not condense in the external tubing.

Figure 16A:
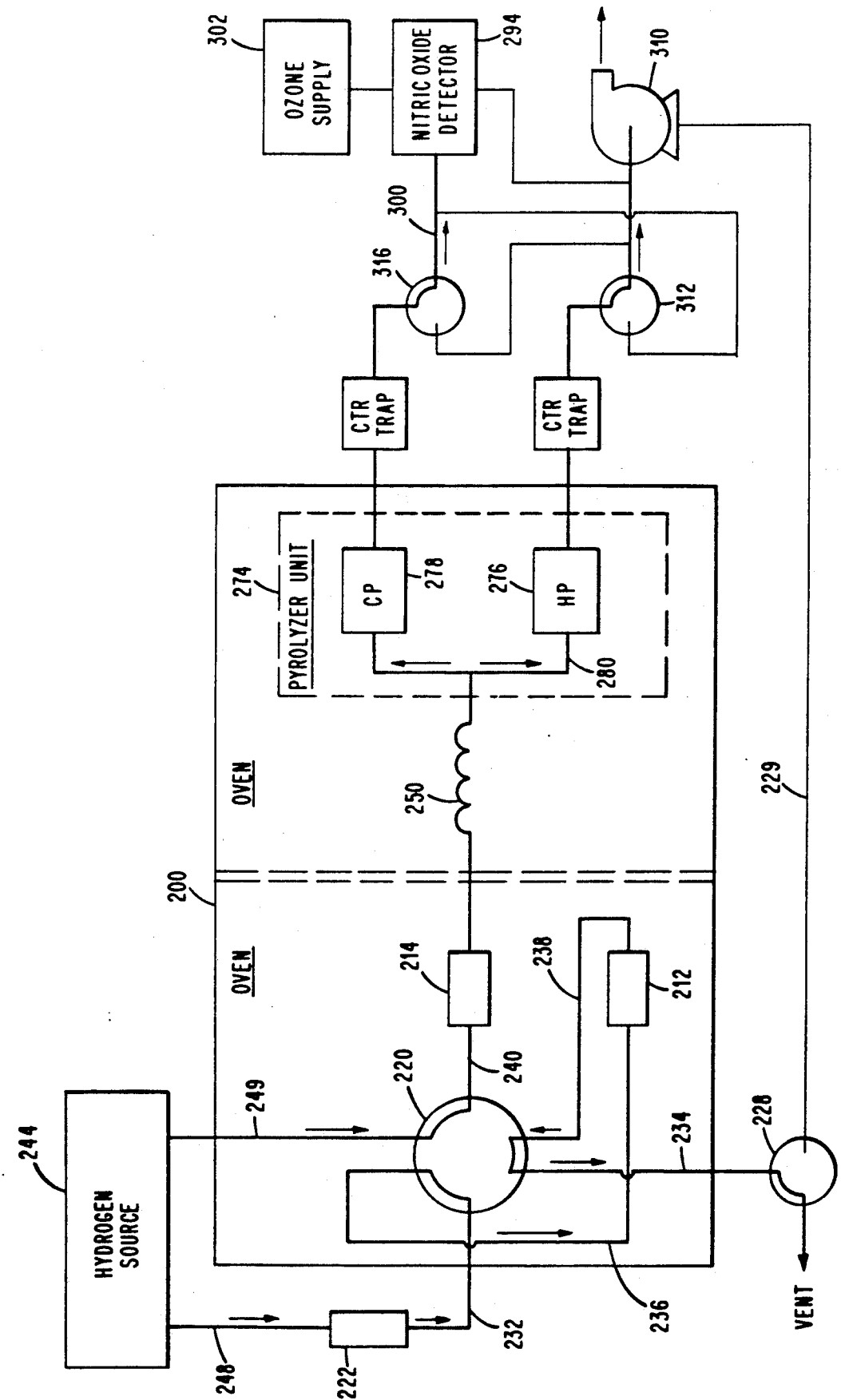
FIGS. 16(a) and 16(b) are schematic diagrams of a detector system with two cold spots and illustrating conduits and valving associated with flows of gases and vapors during sampling and analysis.
Figure 16B:
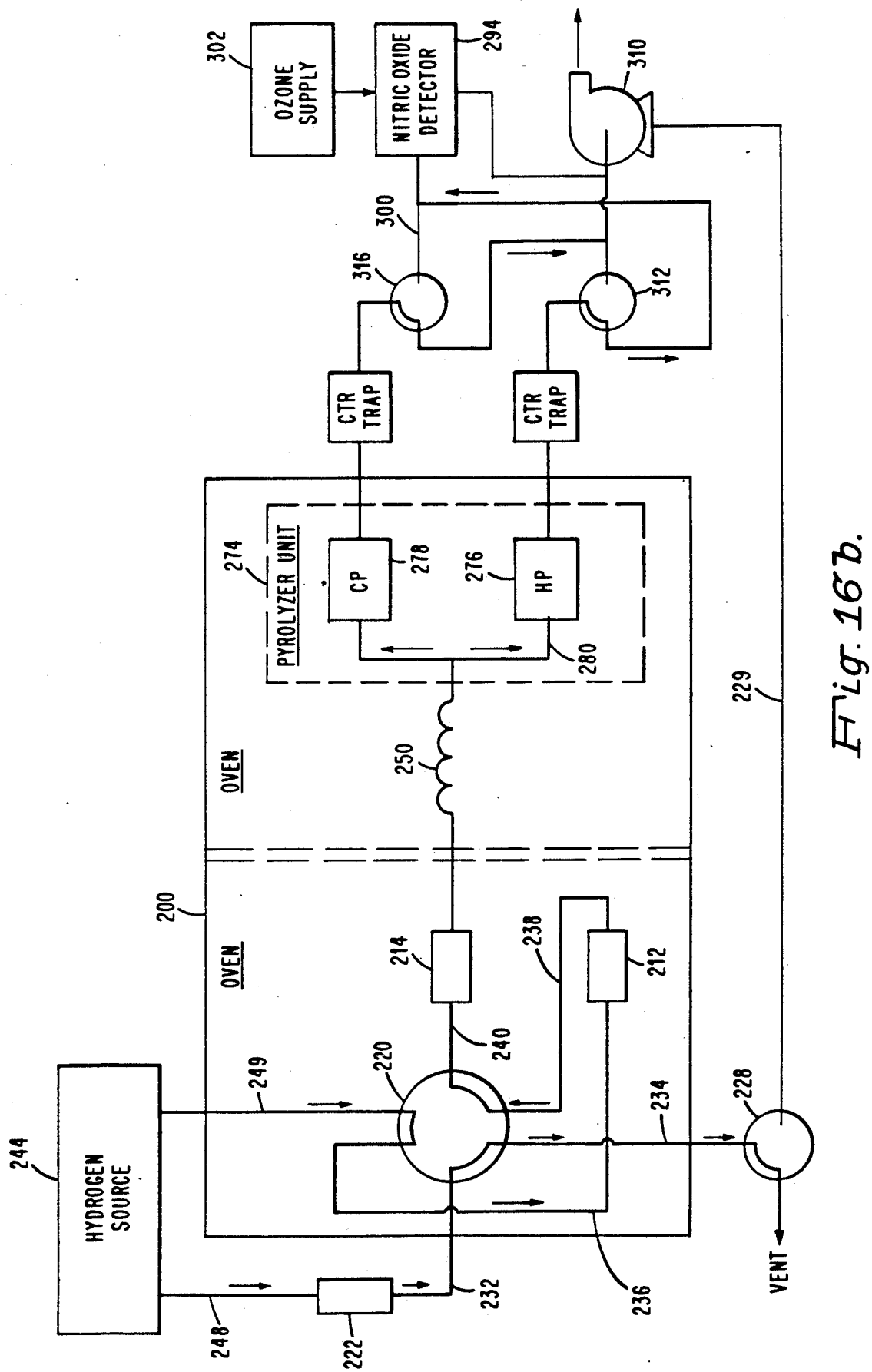

A schematic diagram of a system 210 suitable for rapidly and selectively detecting explosives vapors at high sensitivities (FIGS. 16(a) and 16(b)) illustrates a preferred arrangement of flow lines and valving associated with two series-connected cold spots 212 and 214.

In the system 210 the cold spot 212 and 214 may include the tubes 188 and 203 described hereinabove, and the cold spots 212 and 214 are enclosed by the same cold block, which for simplicity is not shown in FIG. 16.

Flows of gas samples, carrier gas, and explosive vapors through the system 210 illustrated in FIG. 16 are regulated by various multi-position valves whose settings are controlled by a microprocessor 28 (see FIG. 1) which also controls operation of other components of the system such as the various heaters used in desorbtion of explosives vapors, vacumm pumps, pyrolyzers, the nitric oxide detector, and the gas chromatograph. As best shown in FIG. 16(b), a multi-port (e.g. 6-port) valve 220 regulates flow along flow lines 232 and 234 between a collector 222 which is contained within a collector/desorber chamber (FIG. 12) and a valve 228, which may vent the flow to atmosphere or pass the flow to a vacuum pump 310 along flow line 229. The valve 220 also regulates flow through the cold spots 212 and 214 along flow lines 236, 238, and 240. The valve 220 is also connected to a source of carrier gas 244 by a flow line 248, and the flow line 248 may extend through a multi-position valve (not shown) to permit selection of carrier gas of different pressures from the carrier gas source 244—e.g., pressures ranging from about 4–12 psig.

Hydrogen is preferred as the carrier gas both for desorption of explosives vapors from the collector and the cold spots and for carrying the vapors and their decomposition products through components of the system 210 downstream of the cold spots 212 and 214. Hydrogen is readily available for example, by electrolysis of water, and does not react with explosives vapors or nitric oxide, and its low molecular weight facilitates rapid flow through the system 210 and hence fast detection of explosives. It also provides output signals with high resolution (sharp peaks) of output signals. The use of hydrogen rather than air avoids response of the detection system to nitrogen-containing compounds other that those which contain the —NO or —NO$_2$ moiety since, with hydrogen, there in no oxygen available to convert such compounds to NO. Moreover, although hydrogen is reactive with air and more reactive yet with ozone and thus would be thought by others to be unsuitable for use in an air sampling system and for carrying nitric oxide into a detector to which ozone is also introduced as a reactant, use of hydrogen in the system disclosed herein has proven quite effective and trouble-free. This is believed due to the small amounts of hydrogen used relative to the concentrations required for explosions and because the reactions in the chemiluminescent NO detector occur at low pressures created by a vacuum pump.

Air, though lacking the above described advantages of hydrogen, is readily available and may be used for desorption of vapors from the collector. However, a non-oxidizing carrier gas is needed for desorption from at least the second the cold spot. Helium is an alternative to hydrogen, though it lacks hydrogen's very high diffusivity and is not generally readily manufacturable on site as needed.

The system of FIGS. 16(a) and 16(b) is used to move vapors of specific compounds such as explosives from the collector 222 to the cold spot 212, then to the cold spot 214 and thereafter into a gas chromatograph 250 in a series of steps as follows. (It should be understood that, as mentioned earlier, the collector 222 may trap explosives vapors while positioned either in a collector/desorber chamber forming part of an overall detection system having interconnected subsystems or while mounted in a portable sample gun from which the collector can be removed and transferred to a desorber chamber.) First, with the valve 220 positioned as shown in FIG. 16(a) to permit flow from the collector 222 to the cold spot 212, the collector 222 is heated and hydrogen gas is passed at a predetermined pressure (e.g., 5–9 psig) from the carrier gas source 244 along the flow line 248 and sweeps explosives vapors from the collector 222. The vapors and hydrogen carrier gas pass along flow lines 232 and 236 at a relatively moderate flow rate (e.g., 50 cm$^3$/minute) into the cold spot 212 (maintained at a low temperature by its cold block). The cold spot 212 traps and concentrates the explosives vapors and the carrier gas exhausts from the system 210 along the flow line 234. Independently, carrier gas, also preferably hydrogen, from the source 244 may be directed at a selected pressure (e.g. about 9–12 psig) along flow lines 249 and 240 to purge the cold spot 214, or, if the detector system 210 is being used for analyzing samples in succession and the cold spot 214 already contains a concentrated sample, to sweep explosives vapors from the cold spot 214 (as it is being flash-heated) into the gas chromatograph 250.

After explosives vapors have been moved from the collector 222 and concentrated in the cold spot 212, the valve 220 is switched to the position shown in FIG. 16(b) and the explosives vapors are desorbed from the cold spot 212 and further concentrated in the cold spot 214. To accomplish this the cold spot 212 is rapidly heated and hydrogen carrier gas from the source 244 sweeps the explosives vapors from the cold spot 212 into the smaller cold spot 214 whose relatively cold GC material traps and concentrates the vapors.

GAS CHROMATOGRAPH

After vapors of specific compounds have been concentrated in the cold spot 214, the vapors are "fired" to the gas chromatograph 250 by a final desorption effected by rapid heating of the cold spot 214 while carrier gas is flowed through it. The gas chromatograph 250 separates different compounds such as explosives one from another and from other compounds which could interfere with their detection, again without decomposing the explosives. Preferably, the gas chromatograph 250 includes a relatively short analytical section of tube (typically a coiled tube about 12 feet long) and is a high-speed device i.e., explosives vapors injected into its inlet end are rapidly separated and various components emerge from its inlet according to specific calibrated retention times, with all explosives vapors chromatographed in less than about 25 seconds. A suitable gas chromatograph tube is a quartz capillary tube about 12 feet long and 0.32 mm inner diameter and whose inner surface is covered with a GC material which may be the same as that employed in the collector 222 and the cold spots 212 and 214. The tube is enclosed in an oven 268 which maintains a uniform temperature such as about 170° C. in the tube suitable for separation of the explosives vapors through the tube without decomposition of the vapors.

The use in the gas chromatograph 250 of (1) a small diameter tube with thin coatings, (2) hydrogen as a carrier gas (providing high diffusivity), and (3) injections into the gas chromatograph (GC) of very small volumes of gas sample (due to the concentrating or prefocussing action of the cold spots) results in fast gas chromatography—i.e., gas chromatography which is completed in about 25 seconds to as low as about 4 seconds. Additional speed, so as to effect a very fast GC time of one second or less, has been demonstrated by rapid temperature programming of gas chromatograph tube—that is, a rapid, controlled heating of the tube so as to successively move various explosives of different vapor pressures through the GC tube as the temperature is ramped up or increased in a prescribed manner. These fast, and very fast, gas chromatography techniques, which are discussed in more detail hereinafter relative to a detection system including two series-connected pyrolyzers, are applicable not only to detection of explosives vapors and of other compounds but also in analytical lab procedures requiring gas chromatography. They provide at least two advantages. First they permit analyses to be performed in seconds rather than the several minutes (e.g., 8-40 minutes) required previously for an analysis which includes gas chromatographic separation. Second, they reduce the peak width of signals produced in a detector downstream of the GC, which both (1) enhances selectivity (sharp, spike-like peaks being easier to distinguish that wide, spread-out peaks) and also (2) increases sensitivity of detection (since the peak amplitude increases so as to maintain same overall signal area).

PYROLYZER UNIT

The output of the gas chromatograph 250 is passed into a pyrolyzer unit 40 which functions to decompose explosives vapors to yield nitric oxide gas. A preferred pyrolyzer unit 274 (FIGS. 16(a) and 16(b)) includes two pyrolyzers 276 and 278 of similar size and flow capacity and which are downstream of a heated flow splitter 280 which serves to divide the effluent of the gas chromatograph 250 into substantially equal flows. The use of dual pyrolyzers, each operable at a different temperature, substantially enhances the selectivity of the explosives detector, as will be explained hereinafter.

The pyrolyzer 276 is operated as a high temperature pyrolyzer, typically at temperatures in the range of about 700 to 1000 degrees C., typically about 750 degrees C., while the pyrolyzer 278 is heated to substantially lower temperatures—e.g., in the range of about 160 to 250 degrees C., typically about 200 degrees C. Rather surprisingly, and of considerable benefit in the selective detection of explosives, it has been found that the use of silver as a surface in the low temperature pyrolyzer 278, in the presence of hydrogen, selectively produces nitric oxide gas from nitrite esters and nitramines at temperatures considerably lower than those required to produce nitric oxide from other nitrogen-containing compounds such as those with C—NO$_2$ or N—NO bonds. Because of this, nitrite esters and nitramines, which contain the structure R—N—NO$_2$ and R—O—NO (where R may be an organic radical or any other suitable element or combination of elements) and include explosives such as EGDN, NG, PETN, and RDX, and HMX, can be detected in an NO detector after decomposition at temperatures of about 200° C. without interference from other nitrogen-containing compounds (which do not decompose to produce NO at such low temperatures).

At the present time only silver appears to be able to promote pyrolysis of certain explosives at temperatures at or below 200° C. Metals such as gold, platinum, nickel, and molybdenum, though they reduce somewhat the temperatures required for pyrolysis of explosives when compared with non-metallic (quartz or ceramic) surfaces in a pyrolyzer, still must operate at temperatures in excess of 300° C. to decompose any explosives to yield nitric oxide. At such higher temperatures, however, nitrosamines and other non-explosives are also pyrolyzed, increasing the risk of false signals.

Figure 17:
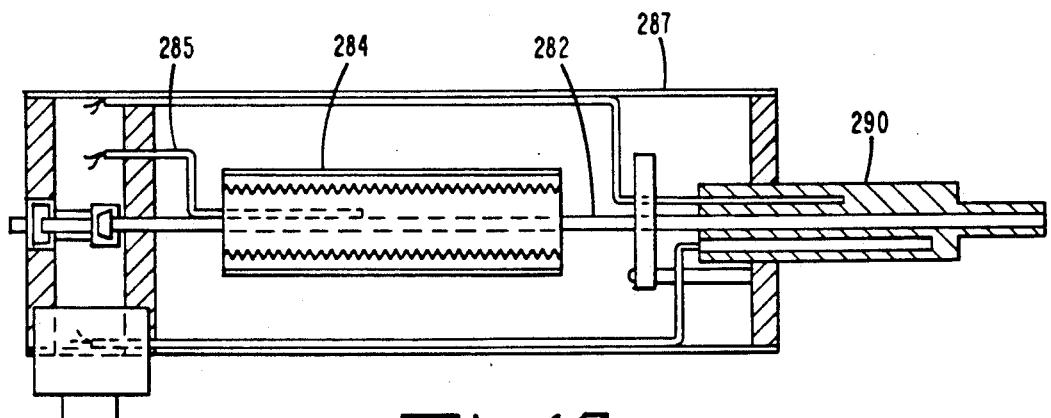
FIG. 17 is a side view of a pyrolyzer of the detection system.

Accordingly, the low temperature pyrolyzer 278 (FIG. 17) preferably comprises a tube 282 of silver or has an inside surface which contains silver. A preferred tube is a silver tube about of 0.4 cm inner diameter and about 35 cm in length. The tube may also contain a coiled wire of silver to provide additional surface area, and a silver wire or silver frit may be used in a quartz tube or ceramic tube so long as adequate silver surface is available to contact samples passing through the tube. The tube 282 is coupled to a heater such as an electrical resistance heater 284 which surrounds a working length (e.g. 15 cm) of the tube 282 and maintains the tube 282 at a preselected temperature as sensed by a centrally located thermocouple 285, so that vapors passing through it are heated as they pass rapidly through the tube—i.e., in a fraction of a second. The working portion of pyrolyzer 278 may be enclosed in an aluminum housing 287 and a heated interface 288 may surround the inlet end of the pyrolyzer tube 282 extending through an endwall of the housing 287 so as to prevent sticking of vapors during their transport from the gas chromatograph 250 to the working portion of the pyrolyzer 278.

The precise reactions by which silver promotes the selective production of nitric oxide from nitrite esters and nitramines at temperatures markedly lower than those required to produce nitric oxide from C—NO$_2$ and N—NO compounds are not fully understood. It is hypothesized that the mechanism involves the chemisorption of the O—NO$_2$ or N—NO$_2$ portion of the nitrite ester or nitramine onto silver and a chemical reaction which produces silver nitrite according to reaction 1 below (for a nitrite ester, where R is an organic group).

$$R-O-NO_2 + Ag \rightarrow AgNO_2 + R-O \text{ (chemisorbed)} \quad (1)$$

The silver nitrate then decomposes in the presence of hydrogen to produce nitric oxide, water, and elemental silver (reaction 2), and the remaining fragment of the nitramine or nitrite ester reacts with hydrogen to produce an alcohol or amine (reaction 3), as follows:

$$AgNO_2 + H_2 \rightarrow Ag + NO + H_2O \quad (2)$$

$$H_2 + 2R-O \rightarrow 2R-OH \quad (3)$$

Chemisorption of C—NO$_2$ compounds onto silver apparently does not occur because the carbon lacks a lone pair of electrons. N—NO compounds do not chemisorb because apparently a nitro (—NO$_2$) group is required for proper steric and electronic interaction with silver. The high temperature pyrolyzer 276 includes a tube 286 of dimensions and flow capacity similar to those of the low temperature pyrolyzer 278 but which is formed of, or lined with, ceramic such as aluminum oxide. A quartz tube may also be suitable. A heater 290 surrounds the tube 286 and is operable to maintain a temperature in the range of about 700 to 1000 degrees C. of the tube 286 and its contents. At these elevated temperatures vapors of known explosives as well as vapors of many nitrogen-containing compounds such as nitrosamines, perfumes, etc., will, if present, decompose to produce NO. Timewise separation of the various compounds, along with interference-free detection of nitrite esters and nitramines decomposed in the low temperature pyrolyzer 278, permits accurate identification of explosives vapors.

NITRIC OXIDE DETECTOR

Figure 18:
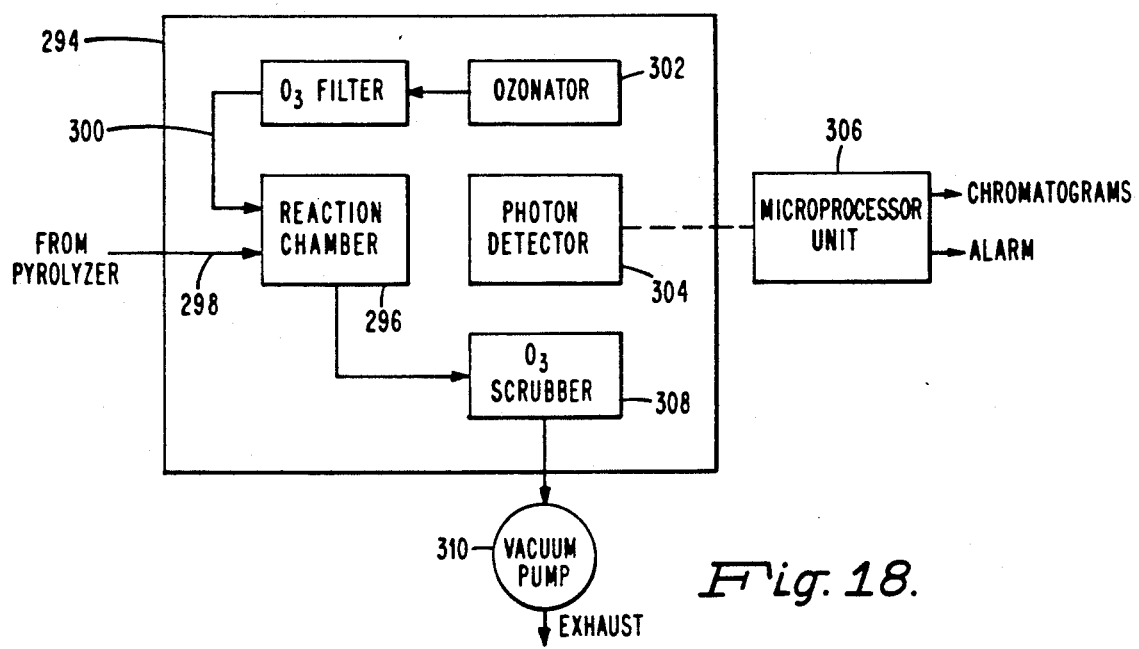
FIG. 18 is a view of an ozone-based chemiluminescence NO detector suitable for use in the vapor detection system.

The nitric oxide detector 294 to which the output of a selected pyrolyzer 276, 278, is directed may be any suitable NO analyzer of high sensitivity and high speed, and is preferably a high speed instrument utilizing known principles of chemiluminescence, photoionization, or electron capture. The detector which is currently most preferred is a chemiluminescence-based analyzer similar to, but substantially upgraded from, the type disclosed in U.S. Pat. No. 3,996,002, whose disclosure is incorporated herein by this reference to that patent, and which is used as a component of the Model 502 TEA Analyzer available from Thermedics Inc. of Woburn, Mass. The chemiluminescence nitric oxide detector 294 (FIG. 18) includes a reaction chamber 296 into which is fed along lines 298 and 300, respectively, decomposition products of either pyrolyzer 276, 278, and ozone from a suitable supply such as an ozonator 302, a known device which forms ozone by bombarding oxygen in air with electrons to form atomic oxygen, some of which combines with molecular oxygen to form ozone. Reaction of the ozone and any nitric oxide present in the output of the selected pyrolyzer 276 or 278 in the chamber produces $NO_2$, an excited form of $NO_2$ which rapidly decays, emitting radiation in a narrow wavelength range such as 0.6–2.8 microns which is detected by a photodetector or photondetector 304. The resulting signals are fed to a microprocessor unit 306 which produces timewise signal traces or chromatograms on a chart recorder, and the processed signals can also be displayed and if desired used to trigger alarms upon the detection of NO from explosives vapors. The reaction products together with excess ozone and carrier gas, pass through an ozone scrubber 308 and are exhausted through a vacuum pump 310.

To provide fast detection required for near real-time analyses by the disclosed detection system the preferred chemiluminescence detector 294 includes an $NO/O_3$ reaction chamber with a small volume and a shape which allows reactants to flow quickly through the detector—i.e., as "plug" flow. A reaction chamber shaped to provide a small depth of gas viewed by its photodetector produces a reduced level of DC noise from emissions of excited oxygen and ozone. A chamber with a small internal wall surface area, and including polished wall surfaces, reduces collisions with surfaces and thus the level of AC noise. Because signal level is unaffected by such modifications, the sensitivity of detection is increased. The detector 294 also is operated under vacuum—e.g., at a pressure of about 1–2 torr, which provides low effective volumes of the reaction chamber. Fast reaction times, as well as higher sensitivities, are also promoted by the delivery to the reaction chamber of high concentrations of ozone, for example, by supplying ozone as the output of two or more series-connected ozonators or of a single ozonator through which the ozone output is recycled to increase ozone concentration. Tests of two and three ozonators connected in series have shown large increases in sensitivity of the NO detector 294. The above-described combination of features, together with fast electronics in the microprocessor unit 28 processing signals from the detector 294 and controlling various components of the system, provides rapid, selective detection of nitric oxide at high sensitivities.

OPERATION OF THE SYSTEM

Figure 19:
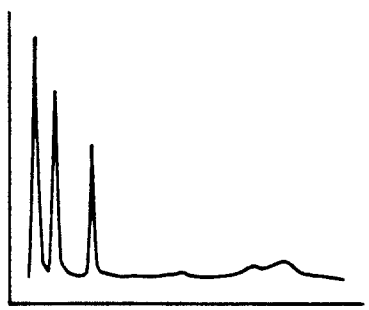
FIG. 19 is a sketch of a chromatogram which would result from analysis in an NO detector of the products of decomposition of a gas sample in a low temperature pyrolyzer.

Reference is made to FIGS. 16(a) and 16(b) for further discussion of the operation of the pyrolyzer unit 274 and the NO detector 294. Sample output from the gas chromatograph 250 is divided by the flow splitter 280 into two substantially equal portions which pass through the pyrolyzers 276 and 278. With the system 210 in the "low temperature" mode (FIG. 16(a)), high speed (e.g. 5 millisecond) valves 312 and 316 downstream of the pyrolyzers 276, 278 are set to dump the output of the high temperature pyrolyzer 276 through the vacuum pump 310 and to pass the output of the low temperature pyrolyzer 278 to the NO detector 294. Provided that the sample included nitrite esters and/or nitramines, the resulting chromatogram, sketched in FIG. 19, will include well-defined peaks, each of which is identifiable, by prior calibration of explosives vapors of known composition, as a specific explosive. Because of the compounds separated by the gas chromatograph 250, only nitrite esters and nitramines decompose in the low temperature silver-containing pyrolyzer to produce NO at the low operating temperatures of the pyrolyzer 278, only a few well-separated peaks will be present. Thus the identification of explosives is rather simple and clear.

It should be understood that the "low temperature" modes of operation of the system 210 are shown in FIGS. 16(a) and 16(b), respectively, only because those two figures offer a convenient means of illustrating the two modes. FIGS. 16(a) and 16(b) are not intended to indicate that these modes occur at times coinciding with particular settings of the valve 220 or of desorbtions from the collector 222 or cold spots 212, 214. Instead, the "low temperature" and "high temperature" modes are timed to occur (by action of the microprocessor unit) at times preselected so as to pyrolyze vapors of interest following their gas chromatographic separation.

Figure 20:
FIG. 20 is a sketch of a chromatogram which would result from analysis in an NO detector of the products of decomposition in a high temperature pyrolyzer.

When the valves 312 and 316 are switched to operate the pyrolyzer unit 274 in the "high temperature" mode (FIG. 16(b)) the output of the low temperature pyrolyzer 278 is dumped through the vacuum pump 310 and the output of the high temperature pyrolyzer 276 is passed to the NO detector 294 for analysis. The resulting chromatogram, sketched in FIG. 20, will include the same peaks as were present in the "low temperature" chromatogram of FIG. 19 and may include additional peaks indicative of nitrogen-containing compounds (e.g., nitrosamines, perfumes) which decompose to produce nitric oxide at the higher temperatures maintained in the pyrolyzer 276. Certain of the additional peaks in FIG. 20 are identifiable as explosives by their position in the chromatogram relative to prior calibrations. The peaks for explosives previously identified in FIG. 19 need not be separated from signals of other compounds which could otherwise interfere with detection of explosives.

TEST DATA

FIGS. 21(a) through 21(q) are chromatograms from tests of mixtures of known nitrogen compounds, some of which were explosives, conducted to check the operation of the pyrolyzers 276 and 278. The samples were injected into a gas chromatograph, whose output was directed into a selected pyrolyzer and then analyzed in an NO detector 294. The gas chromatograph included a glass column about six meters in length and with an inner diameter of 0.25 millimeters and a coating of DB5 material (J & W Scientific) of about one micron thickness, and which was enclosed in an oven maintaining a temperature of about 150 degrees C. Hydrogen at a supply pressure of 5 psig was used as a carrier gas and the pressure in the chemiluminescent reaction chamber of the NO detector was about 1 torr.

FIG. 21(a) is a chromatogram resulting from testing of a sample containing 0.2 microliters (one picomole) of the explosives NG, DNT, TNT, PETN, and RDX and which was analyzed after passing through the gas chromatograph 250 and the low temperature pyrolyzer 278 which included a silver tube, and a CTR trap (see discussion later in this subsection of the traps 330, 332 (FIG. 16)). For the tests whose results are shown in FIGS. 21(a) through 21(i) the temperatures of a 6-inch heat zone of the pyrolyzer 278 and a 12-inch heat zone immediately downstream of the 6-inch zone were held at about 165 and 180 degrees C., respectively.

The FIG. 21(a) chromatogram shows that NG, PETN, and RDX, the explosives which are nitrite esters or nitramines, produced clear peaks and thus can readily be detected and identifed by prior calibrations at the relatively low temperatures employed. DNT and TNT, which are C-nitro compounds (i.e., have C—$NO_2$ bonds) produced no detectable signals, indicating, as expected, that they were not decomposed in the low temperature pyrolyzer to yield NO. Similar results (not shown) were obtained in tests of these explosives at a somewhat lower temperature (successive heat zones were maintained at 149° C. and 148° C.).

Chromatograms of selected nitrogen compounds which are not explosives (FIGS. 21(b) through 21(i)), such as various nitromusks which are present in perfumes, and pyrolyzed at about 180 degrees C. and under the same conditions as the above-mentioned sample of five explosives, show no clearly identifiable signal peaks (initial peak at left side of chromatogram is a transient "front"). The substances injected were as follows: 21(b)—0.2 microliters (1440 ng) of musk tibetene in dimethyl ketone solvent (DMK); 21(c)—0.2 microliters (856 ng) musk ketone (DMK); 21(d)—0.2 microliters (3600 ng) hydroxycitronella schiff base (DMK); 21(e)—0.2 microliters (1320 ng) musk ambrette (DMK); 21(f)—0.2 microliters (1020 ng) trifluralin (a herbicide) (DMK; 21(g)—0.2 microliters (1500 ng) moskene (DMK); 21(h)—0.2 microliters (1910 ng) musk xylol (DMK); 21(i)—0.2 microliters (1910 ng) musk xylol (DMK). The absence of peaks indicates that no detectable decomposition of these compounds to NO occurred in the low temperature pyrolyzer and hence that these compounds would not interfere with detection of explosives which are nitrite esters or nitramines during time intervals wherein the output of the low temperature pyrolyzer was directed to the NO detector.

FIGS. 21(j) through 21(s) are chromatograms from tests of various samples passed through a quartz tube pyrolyzer about nine feet long heated to temperatures ranging from 300 degrees C. to 800 degrees C. At pyrolyzer temperatures of 300 degrees C. (FIGS. 21(j) and 21(k)) and 450 degrees C. (FIGS. 21(n) and 21(o)) little or no detectable response occurs for any of the explosives tested, (1 picomole each of NG, DNT, TNT, PETN, and RDX), with the only distinguishable peaks (for PETN and RDX) having amplitudes just slightly above the noise level. The contrast between this lack of response and the clear signals for certain explosives at lower temperatures when silver is used in a pyrolyzer confirms the efficiency of silver in promoting the decomposition of selected compounds to yield NO. Also, the observable peaks in FIG. 21(m) for the mixture of nitrosamines pyrolyzed at 300 degrees C. (0.2 microliters of nitrosodimethylamine, nitrosopyrolidine, nitrosomethylaniline, nitrosonornicotine, and 4-(methylnitrosamino)-1-(3-pyridyl)-1-butanone) and for the mixture of perfumes (0.2 microliters of muskambrette, musk ketone, musk tibetene, musk xylol, moskene, hydroxycitronella, and schiff base) pyrolyzed at 450 degrees C. (FIGS. 21(p) and 21(q)) demonstrate the potential for interferences due to these compounds as pyrolyzer temperatures are increased. No discernable peaks are noted in FIG. 21(l), a test of the same mixture of perfumes in the quartz pyrolyzer operated at the lower temperature of 300° C.) Thus at 800 degrees C., a temperature at which all explosives (including DNT and TNT) have decomposed in a quartz pyrolyzer to yield No (see FIGS. 21(r) and 21(s)) and which approximates those temperatures formerly required for analysis of all explosives by decomposition to, and detection of, nitric oxide gas, there could be difficulty distinguishing between the peaks of explosives and those of non-explosives which have similar retention times in the gas chromatograph. However, because several explosives (those which are nitrite esters and nitramines) can be readily detected after decomposition in the low temperature silver pyrolyzer 278, only a relatively few explosives need be distinguished from potential interferents in the chromatograms resulting from decompositions in the high temperature pyrolyzer. Thus the explosives of interest can be clearly identified by using the low and high temperature pyrolyzers in sequence.

In addition to the selectivity provided by the collector, cold spots, gas chromatograph, and the pyrolyzers disclosed herein, further avoidence of interferents and hence enhanced selectivity to explosives detection may be furnished by traps 330 and 332 in the flow lines 336 and 338 between the pyrolyzers 276, 278, and the valves 312, 316 controlling output flow of these pyrolyzers (see FIG. 16). The traps 330 and 332 are preferably cartridges containing a granular material such as an alumino-silicate molecular sieve material of selected pore size, and are effective to pass NO but trap organic compounds, chlorinated solvents, and sulfur compounds which could otherwise produce responses in a chemiluminescence NO detector which would interfere with proper detection of NO. Suitable traps or filters are described in U.S. Pat. No. 4,301,114, whose disclosure is incorporated herein by this reference to it, and are available as CTR traps from Thermedics Inc. of Woburn, Mass.

A preferred method of operating the detector system 26 to rapidly detect vapors of selected explosives of a sample is to monitor products of the low temperature pyrolyzer 278, during time intervals corresponding to those for which the explosives vapors emerging from the gas chromatograph 250 are known from prior calibrations to be only nitramines, nitrite esters, and other explosives which decompose in the low temperature pyrolyzer 278, and to detect products of the high temperature pyrolyzer 276 for the remaining time. This is readily accomplished by appropriate switching of the valves 312 and 316 at selected times controlling their operation. For example in analysis of a sample for the explosives EGDN, NG, DNT, TNT, PETN, and RDX, which emerge from the gas chromatograph 250 in the above-recited order and produce peaks on a chromatogram at specific known times, only DNT and TNT require pyrolysis in the high temperature pyrolyzer 276. Thus, sample analysis is performed by (a) initially operating in the low temperature mode to produce signals indicative of EGDN, then NG, if present, (b) at a predetermined time switching the high speed valves 312 and 316 to operate in the high temperature mode so as to detect DNT, the TNT, and (C) at a second predetermined time, switching the valves 312 and 316 to obtain signals from PETN and RDX, if present in the sample. From the above-described sequence of operations a three-section chromatogram is produced, and the chromatogram provides signal information over essentially all of the 20-30 second time interval of interest—i.e., little or no information is lost in switching between high and low temperature modes because the valves 312, 316 operate at high speeds (e.g., five milliseconds) and because equal portions of the sample are continually flowing through each pyrolyzer 276 and 278 even when the products of one are exhausted without first being analyzed in the NO detector 294. Low temperature operation for two of the three portions of the chromatogram avoids possible interfering signals in those portions from compounds which pyrolyze at temperatures above the operating temperature of the low temperature pyrolyzer 278.

ALTERNATE SYSTEMS

Figure 22:
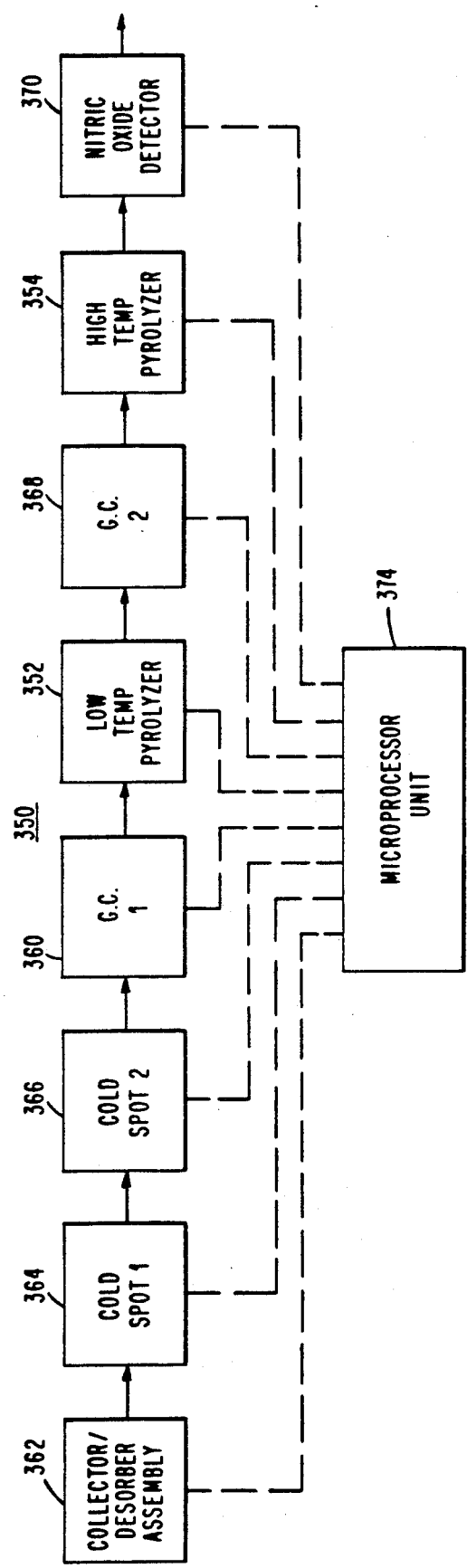
FIG. 22 is a block diagram of a vapor detection system which includes two pyrolyzers and two gas chromatographs in a series-connected arrangement.

FIG. 22 shows, in block diagram form, an alternative vapor detection system 350 in which two pyrolyzers 352 and 354 are connected in series rather than in the parallel configuration illustrated in FIGS. 16(a) and 16(b). The series arrangement, together with an additional selective element or gas chromatograph 368 between the pyrolyzers 352 and 354 provides selectivity by time-shifting signals from various compounds, including certain explosives and various other compounds which could otherwise interfere with detection of explosives whose signal are not shifted. The system 350 avoids valve shifting between pyrolyzers required in a "parallel pyrolyzer" arrangement and is thus less complex. Because the flow is not split between two pyrolyzers, but the entire flow passes through both, the system also offers higher sensitivity than a comparable "parallel" system. Additional improvements in sensitivity result from the very high speed operation permitted by this arrangment. This may be important in detecting vapors of explosives having low vapor pressures (e.g., plastics) and whose airborne concentrations may be as low as one part in $10^{15}$ or $10^{16}$.

A gas sample which has been collected from the air is processed in the system 350 by being desorbed from a collector in collector/desorber assembly 362 then concentrated in a single cold spot or, if two cold spots 364 and 366 are employed, successively in cold spot 364, then cold spot 366. The desorbtion may be performed at or below atmospheric pressure by use of vacuum, which reduces the time and amount of carrier gas (e.g., hydrogen) required, and, if so, a flow restrictor may be provided between the carrier gas supply and the collector to assist in controlling flow. The flash-heated output of cold spot 366 is separated in the selective element or gas chromatograph 360, which may include a 0.32 mm ID quartz GC tube 2-6 feet in length and coated with a 1-2 micron coating of DB5 GC material, and is passed with its non-oxidizing carrier gas (preferably hydrogen) into the low temperature pyrolyzer 352. The low temperature pyrolyzer 352 may be a silver-containing pyrolyzer operable at a temperature in the range of about 160° to 250° C. so as to decompose nitramines and nitrite esters to produce NO without decomposing other explosives, perfumes, nitrosamines, etc. Alternatively the pyrolyzer 352 may be a non-silver pyrolyzer—e.g., a quartz pyrolyzer or nickel-containing pyrolyzer, operable at a temperature, such as about 275° C., sufficient to decompose nitramines and nitrite esters to produce $NO_2$, again without decomposing other explosives, perfumes, nitrosamines, etc. Either pyrolyzer may be about 10 cm in length and of small diameter—e.g., a quartz capillary tube of 0.32 mm ID extending through electric-resistance-heated needle—stock stainless steel tube. The NO or $No_2$ produced in the low temperature pyrolyzer 352 passes through the gas chromatograph 368 very rapidly, essentially without being retarded at all by the active coating of its analytical column (which may be a 0.32 mm quartz GC tube 2-6 feet long and with a 1-2 micron coating of DB1 GC material). Other compounds, particularly perfumes, nitrosamines, explosives vapors, etc., are delayed in passage in the gas chromatograph 368 according to their GC- separation characteristics.

Figure 23:
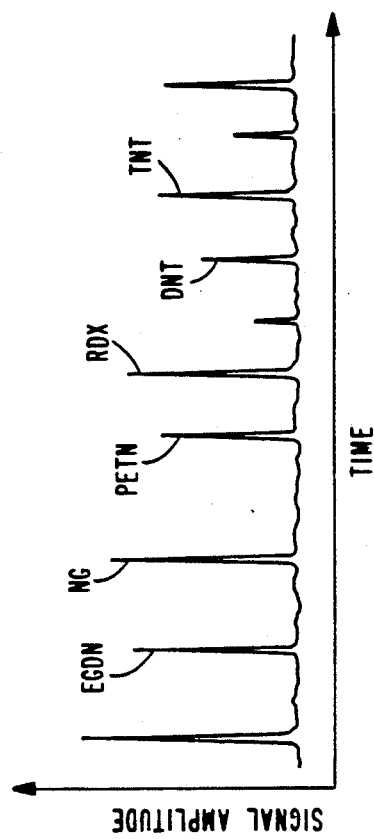
FIG. 23 is a sketch of a timewise trace of output signals from a detection system such as that of FIG. 22.

The high temperature pyrolyzer to which the output of the gas chromatograph 368 passes is preferably a quartz or ceramic pyrolyzer operable at a temperature in the range of 700°-1000° C., typically about 750° C. Essentially all explosives vapors which enter the high temperature pyrolyzer 354, plus and $NO_2$ produced in the pyrolyzer 352 and certain other nitrogen-containing compounds, are decomposed in the pyrolyzer 354 to yield NO. Detection of the NO in the nitric oxide detector 370 allows specific compounds such as explosives to be identified, as illustrated in FIG. 23, a sketch of typical ouput signals which would be produced by the system 350. FIG. 23 shows that explosives which are nitramines and nitrite esters (e.g., EGDN, NG, PETN, and RDX) and which were decomposed in the low temperature pyrolyzer 322) produce peaks in the first portion of the chromatogram, while peaks from other explosives such as DNT and TNT and from non-explosives occur later in time since they have been delayed by the gas chromatograph 368 prior to pyrolysis. The time-shifted signals thus do not interfere with identification of the nitramines and nitrite esters. The time-shifted peaks are also further separated from each another, which may facilitate distinguishing explosive DNT and TNT from non-explosives. Also, because the flow is not divided and hence the NO concentration is not reduced when series-connected pyrolyzers are employed, overall sensitivity of the system 350 is increased up to a factor of two over that of a "parallel pyrolyzer" system.

An important advantage of the series-connected pyrolyzer system 350 of FIG. 22 is that it facilitates very fast analysis by gas chromatography, for detection not only of explosives but also of other compounds of interest. In tests of the system illustrated in FIG. 22, gas chromatographic analyses of explosives have been performed in as fast as 3 seconds following the injection of vapors into the first gas chromatograph 360 by flash-heating or very rapid "firing" of cold spot 366 (in about 10 milliseconds). That is detection of the nitric oxide produced from all explosives in a sample is completed in the 3 second interval after vapors are introduced into the gas chromatograph 360. Such very fast analyses would be difficult, if not impossible, to achieve in a "parallel pyrolyzer" system even with high-speed valves for shifting between pyrolyzer outputs delivered to the NO detector. One reason for this is that in the parallel arrangement at least a few seconds of purge time are required after switching a valve in order to sweep the gas flow out of the flow lines between the valve and the NO detector and to insure that a proper baseline is re-established and that no transient spikes from the valve action are mistaken for signals of vapors to be detected.

To achieve the very fast gas chromatograph (GC) times of 0.5 to 3 seconds, or less, extremely fast injections are required from a cold spot concentrator upstream of a GC, and the GC must be temperature-programmed. For the system configuration of FIG. 22, this means an extremely fast injection from cold spot 366 and that both gas chromatographs 360 and 368 must have their temperatures rapidly increased during selected times (e.g., over intervals of about 10 milliseconds) controlled by the microprocessor unit 374 to quickly release vapors from the chromatographs in a known sequence according to the characteristics of each vapor (i.e., more volatile vapors will be released by their GC coating at a lower temperature-hence earlier in time-than less volatile vapors). A suitable method for accomplishing such temperature programming is to construct gas chromatograph systems by threading the analytical columns of gas chromatographs 360 and 368 through low-mass needle-stock stainless steel tubing, surround this tubing by an air bath, or other means for cooling the tubing and to resistively flash-heat the tubing (while monitoring temperature by sensing the resistance of the metal tubing) to activate the chromatograph column. Such an arrangement permits the temperature of the chromatograph columns to be ramped-up about 100° C. from a base level of about 50°-100° C. in a few milliseconds so that each gas chromatograph completes a chromatographic separation in less than one second. As mentioned earlier, very fast gas chromatographic analyses such as these not only save time but also boost sensitivity of detection since the same mass of each specific vapors is effectively squeezed into a peak of much narrower width. It should also be understood that fast, or very fast gas chromatographic analyses, e.g. of nitramines and nitrite esters, can be performed in a system having a single GC column in series with a cold spot concentrator/injector, pyrolyzer, and specific gas (e.g., NO) detector rather than the dual pyrolyzer, dual GC arrangement of FIG. 22.

ADDITIONAL DATA

Figure 24:
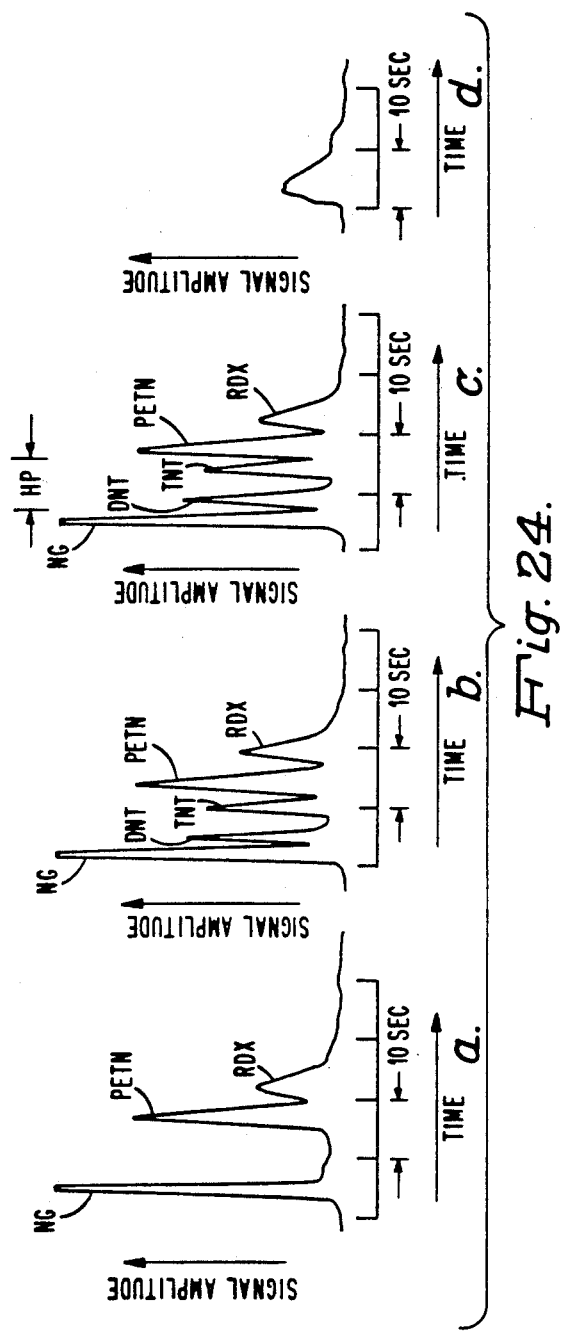
FIGS. 24 and 25 are chromatograms of tests performed on a system similar to that of FIG. 16.
Figure 25:
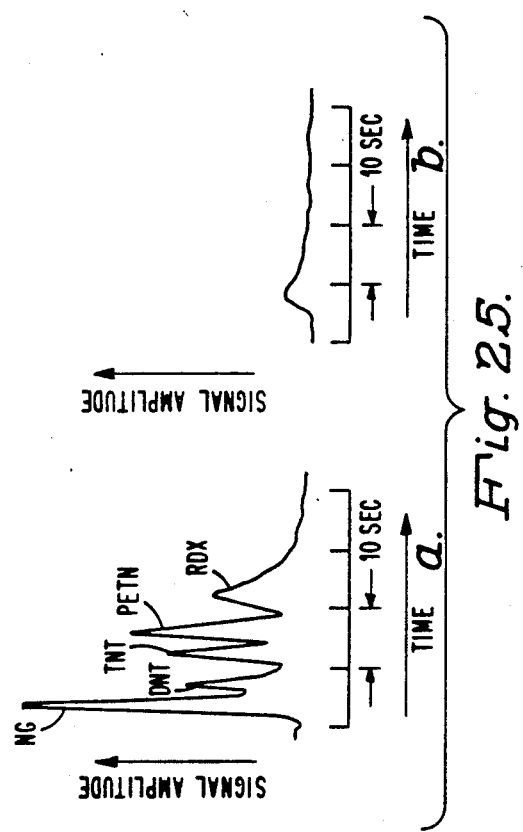

FIGS. 24 and 25 are chromatograms of tests performed as "system checks" or calibrations on a system similar to the system 210 shown in FIGS. 16(a) and 16(b). The signal attentuation factor for each run plotted is 32 and the interval between time marks on the time axis is about ten seconds. The data in FIGS. 24(a), (b), and (c) is from analysis of mixtures of five explosives injected into carrier gas flowing through the system and that of FIG. 25 is from test samples obtained by heating paper towels. System parameters and operating conditions for the tests are summarized in Table 1.

TABLE-1 SYSTEM PARAMETERS AND TEST CONDITIONS

Collector—400 quartz tubes, each 19 mm long and with 0.53 mm. I.D. Internal surface of tubes were coated with 1.5 micron thickness of polymerized methyl or methyl/phenyl silicone as follows: 95% of tubes coated with DB1, 5% with DB5.

Cold Spot Tubes (CS1 and CS2)—Each metal tube contained one quartz tube of working length about 100 mm and with internal surface of quartz tube coated with 1 micron thickness of DB5. CS1 had 0.53 mm ID, CS2 had 0.32 mm ID. Cold spot tubes were maintained at 9° C. except during flash-heating, when CS1 was heated to 152° C. and CS2 was heated to 176° C.

Pyrolyzers (CP and HP)—Each had tube of heated length about 150 mm and 4 mm ID. Low temperature pyrolyzer (CP) was formed of silver and included a coiled silver wire within it. High temperature pyrolyzer (HP) was formed of aluminum oxide. CP operated at 200° C.; HP operated at 750° C.

Gas Chromatograph (GC)—Gas chromatograph (GC) had a quartz tube of length about 15 feet with a 0.32 mm ID, and internal surace of GC tube was coated with 1 micron thickness of DB5. GC was operated at constant temperature 176° C.

Nitric Oxide Detector—NO detector included ozone-based chemiluminescence reaction chamber operated at pressure of 0.38 mm Hg.

| TIME SUMMARY (Analysis with time switching of parallel pyrolyzers) | |
|---|---|
| Time (Seconds) | Event |
| 1 | $H_2$ purge through collector (no heat) |
| 11 | Desorb collector (high lamp heat) |
| 7 | Desorb collector (low lamp heat) |
| 1 | Establish flow through (switched) 6 - port valve - "ready" interval |
| 15 | Desorb CS1 (flash-heat) |
| 1 | Establish flow through (switched) 6 - port-valve-"ready" interval |
| 4 | Desorb CS2 (flash-heat) |
| 6.67 | Time $T_1$ (following initiation of CS2 flash-heat) at which valves between pyrolyzers and NO detector switched so that HP output detected (instead of the CP output detected until valves switched) |
| 8.70 | Time $T_2$ (after $T_1$) at which valves switched so that CP output again detected |
| 45 | Total time data acquisition equipment on - monitoring for peaks |

FIGS. 24 (a), (b), and (c) are results of tests wherein 1.5 microliters of a 10 picomole/microliter mixture of NG, DNT, TNT, PETN, and RDX in acetone were injected into a stream of hydrogen carrier gas ahead of the second cold spot (CS2), followed by detection of the nitric oxide produced after the sample was fired into the gas chromatograph, GC-separated, and pyrolyzed. FIG. 24(d) shows results of a "control" test of an air sample collected by the sample gun (15 second unheated air sample at a flow through the collector of about 2 liters/sec). The absence of any sharp, identifiable peaks in 24(d) indicates no explosives were present. FIG. 24(a), a chromatogram from anlysis of the output of the low temperature pyrolyzer, shows that NG, PETN, (nitrite esters) and RDX (a nitramine) were clearly detected in the low temperature, silver-containing pyrolyzer, while DNT and TNT were not. The approximate sensitivity of detection of PETN for these chromatograms was about 250 picograms—based on detectability of signal having an amplitude twice that of the noise. All five explosives were detected when the output of the high temperature pyrolyzer was analyzed in the NO detector (FIG. 24(b), and these explosives were also clearly sensed (FIG. 24(c)) when the high temperature pyrolyzer was "switched in" for that portion of the analysis (labeled HP) during which DNT and TNT were expected from prior calibrations. It is evident that the system readily detected the five explosives injected. Also, the chromatograms of FIGS. 24(b) and 24(c) are nearly alike; however, had substances such as perfumes or nitrosamines been included in the samples, additional peaks would have been present in the chromatogram from the high temperature pyrolyzer 24(b), likely masking one or more of the peaks for NG, PETN, and RDX, and hence interfering with their detection.

FIG. 25(a) shows data similar to that of 24(c) for analysis of vapors collected by drawing a sample through a collector in the hand-held sample gun, the collector then being transferred to a desorbtion chamber in a portable "cart" containing other components of the detection system. The sample was obtained by heating a paper towel which had been sprayed with a standard solution of the five explosives NG, PETN, RDX, TNT, and DNT, in acetone, the sprayed towel having been stored in a sealed glass jar prior to removal for testing. Heating was performed by flashing lamps of the sample gun (while drawing air through a collector in the gun) a total of eight times for about ½ second durations and at intervals of about ¾ second, then drawing more air (without flashing) for about 5 more seconds. The total air sample was about 11 liters over an 11 second interval. All explosives on the towel were readily detected, as indicated in FIG. 25(a).

FIG. 25(b) shows results obtained when a paper towel similar to that of FIG. 25(a), but containing no explosives, was sampled. No identifiable peaks were detected, confirming that the peaks of FIG. 25(a) were due to the explosives sprayed onto the towel.

It should be understood that solutions of specific compounds to be used for calibrations or system checks can also be sprayed on any suitable sorbent material and sealed in various containers, e. g. a foil-lined plastic pouch. This facilitates system checks even in remote locations and avoids having to inject liquids (by syringe) into the vapor detection system to check its operation.

The detection system and the various components described herein may be embodied in other specific forms. For example, the detector may include, or be operated to employ, a single low temperature pyrolyzer if it is desired to monitor samples for the presence of nitrite esters and nitramines only. Also, the cold spot(s) may be omitted or bypassed if sample collectors of low gas-holding volumes are utilized and increased sample collection times are permitted in a particular detection application. The present embodiments are, therefore, to be considered as illustrative and not restrictive, the scope of the invention being indicated by the appended claims rather than by the foregoing description, and all changes which come within the meaning and range of equivalency of the claims are to be embraced therein.

What is claimed is:

1. Apparatus for concentrating vapors of selected compounds such as explosives comprising:
    a metal tube;
    a coating within said metal tube, said coating when maintained at a first selected temperature being effective to trap vapors of selected compounds from a gas sample passed through said tube without trapping oxides of nitrogen, and when heated to a second selected temperature being effective to release said vapors into a non-oxidizing carrier gas directed through said tube without decomposing said vapors;
    a heater for rapidly heating said metal tube and said coating to said second selected temperature;
    cooling means for maintaining said metal tube and said coating at said first selected temperature during times when said heater is not operating;
    means for directing said gas sample through said tube; and
    means for directing said carrier gas through said tube.

2. Apparatus as in claim 1 wherein said coating is formed of a polymerized silicone material.

3. Apparatus as in claim 1 wherein said coating is applied to the inner surface of said tube.

4. Apparatus as in claim 1 wherein said cooling means includes a block of conductive material surrounding said tube, means for maintaining said block at said first selected temperature, and insulating means for providing electrical and thermal insulation between said metal tube and said block.

5. Apparatus as in claim 4 wherein said insulating means comprises a non-conductive tube between said metal tube and said block.

6. Apparatus as in claim 1 wherein said coating is formed of a material selected from the group consisting of polymerized methyl silicones and polymerized methyl/phenyl silicones.

7. Apparatus as in claim 1 including a tube of non-conductive material extending through said metal tube and wherein said coating is applied to the inner surface of said non-conductive tube.

8. Apparatus as in claim 2 wherein said coating has a thickness in the range of about 0.1 to 5 microns.

9. Apparatus as in claim 3 further including a layer of a dielectric material between said coating and the inner surface of said tube.

10. Apparatus as in claim 1 wherein said carrier gas is hydrogen and said means for directing said gas sample and said carrier gas through said tube includes a source of hydrogen.

11. Apparauts as in claim 1 wherein said heater is operable to heat said tube to a temperature in the range of about 150°-200° C. and said cooling means is operable to maintain said tube at a temperature in the range of about −10° to about 40° C.

12. Apparatus as in claim 1 wherein said metal tube is a first metal tube, said heater is a first heater, and said apparatus includes:
    a second metal tube connected to the outlet end of said first metal tube, said second metal tube having a gas-holding internal volume substantially smaller than that of said first metal tube;
    a coating within said second metal tube effective, when maintained at a third selected temperature, to trap vapors of selected compounds from a gas sample received from said first tube without trapping oxides of nitrogen, and when heated to a fourth selected temperature effective to release said vapors into a carrier gas directed through said second tube without decomposing said vapors;

a second heater for rapidly heating said second metal tube to said fourth selected temperature; and cooling means for maintaining said second metal tube at said third selected temperature during times when said second heater is not operating.

13. Apparatus as in claim 12 wherein said first and third selected temperatures are substantially equal and said cooling means includes a block of conductive material surrounding said tubes, means for maintaining said block at said first selected temperature, and insulating means for providing electrical and thermal insulation between said metal tubes and said block.

14. In an apparatus for detecting vapors of selected compounds such as explosives which includes a gas-pervious collector effective to trap said vapors and a gas chromatograph having an analytical column, and wherein the total gas flow area of said collector is substantially larger than the gas flow area of said analytical column, the combination therewith comprising a cold spot concentrator effective to concentrate vapors received from said collector prior to their entry into said gas chromatograph, said concentrator comprising:

first and second metal tubes connected in series between collector and said gas chromatograph, said first tube having a gas-holding volume substantially larger than that of said second tube and substantially smaller than that of said collector;

an internal coating within each of said tubes, said coating when maintained at a first selected temperature, effective to trap said vapors from a gas stream passed therethrough without trapping oxides of nitrogen and, said coatings of said first and second metal tubes, when heated to second and third selected temperatures, respectively, effective to release said vapors into a carrier gas;

first and second heaters connected, respectively, to said first and second tubes and operable to rapidly heat said tubes to said second and third temperatures;

cooling means for maintaining each metal tube and its coating at said first selected temperature during times when the heater connected to said tube is not operating; and means for directing a gas sample containing said vapors from said collector through said first metal tube; and means for directing a carrier gas through said metal tubes.

15. Apparatus as in claim 14 wherein said cooling means includes a block of conductive material surrounding said tubes, and further including means for providing electrical and thermal insulation between each of said metal tubes and said block.

16. Apparatus as in claim 14 wherein said second metal tube has a portion of the analytical column of said gas chromatograph extending therethrough, said coating within said second tube being applied to an inner surface of said portion of the column.

17. Apparatus as in claim 12 wherein said first metal tube has a glass tube extending therethrough, said coating within said second metal tube being applied to an inner surface of said glass tube.

18. Apparatus as in claim 12 including a source of hydrogen as a carrier gas, a valve connected to said source of carrier gas and to said first and second metal tubes, and a collector connected between said source of hydrogen and said valve, said valve switchable between a first position permitting flow of carrier gas through said first metal tube and a second position permitting flow of carrier gas through said first and second metal tubes.

19. Apparatus as in claim 10 wherein said means for directing said gas sample and said carrier gas through said tube includes a vacuum pump in communication with the downstream end of said tube.

20. Apparatus as in claim 14 wherein said carrier gas is hydrogen and said means for directing carrier gas and said gas sample through said first metal tube includes a source of hydrogen in communication with the upstream end of said first metal tube and a vacuum pump in communication with the downstream end of said first metal tube.

* * * * *